(12) United States Patent
Bavari et al.

(10) Patent No.: US 7,574,340 B2
(45) Date of Patent: Aug. 11, 2009

(54) SMALL MOLECULES AND A PHARMACOPHORE MODEL FOR INHIBITION OF BOTULINUM TOXIN AND METHODS OF MAKING AND USING THEREOF

(75) Inventors: Sina Bavari, Frederick, MD (US);
James J. Schmidt, Frederick, MD (US);
James Burnett, Richmond, VA (US);
Rick Gussio, Frederick, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 219 days.

(21) Appl. No.: 10/935,622

(22) Filed: Sep. 8, 2004

(65) Prior Publication Data

US 2005/0153945 A1     Jul. 14, 2005

Related U.S. Application Data

(60) Provisional application No. 60/501,243, filed on Sep. 8, 2003.

(51) Int. Cl.
*G06G 7/48*     (2006.01)
(52) U.S. Cl. ...................................... 703/11
(58) Field of Classification Search ............... 702/19; 703/11
See application file for complete search history.

(56) References Cited

U.S. PATENT DOCUMENTS 6,531,126 B2     3/2003     Farmer ....................... 424/115
2005/0038246 A1*  2/2005    Arnold et al. ............... 544/262

OTHER PUBLICATIONS

Lacey et al. "Crystal Structure of Botulinum Neurotoxin Type A and Implications for Toxicity," Nature Structural Biology (1998) vol. 5, No. 10, pp. 898-902.*

Schmidt et al. "Type A Botulinum Neurotoxin Proteolytic Activity: Development of Competitive Inhibitors and Implications for Substrate Specificity at the S1' Binding Subsite," FEBS Letters (1998) vol. 435, pp. 61-64.*

Deshpande et al. "Efficacy of Certain Quinolines as Pharmacological Antagonists in Botulinum Neurotoxin Poisoning," Toxicon (1997) vol. 35, No. 2, pp. 433-445.*

Penzotti et al. "A Computational Ensemble Pharmacophore Model for Identifying Substrates of P-Glycoprotein," Journal of Medicinal Chemistry (2002) vol. 45, No. 9, pp. 1737-1740.*

Bajorath, Jurgen "Integration of Virtual and High-Throughput Screening," Nature Reviews Drug Discovery (2002) vol. 1, pp. 882-894.*

Vennerstrom, et al. (1998) "Bisquinolines. 2. Antimalarial N,N-Bis(7-chloroquinolin-4-yl)heteroalkanediamines" J. Med. Chem. 41:4360-4364.

* cited by examiner

*Primary Examiner*—Jerry Lin
(74) *Attorney, Agent, or Firm*—Elizabeth Arwine

(57) ABSTRACT

Disclosed herein is a pharmacophore model for inhibiting Botulinum neurotoxin A metalloprotease activity which comprises a first plane A, a second plane B, a first hydrophobic moiety C, a second hydrophobic moiety D and a positive ionizable substituent E. The pharmacophore model may further comprise a heteroatom in the first plane A. In some embodiments, the distance between the center of the first plane A and the center of the second plane B is about 6.5 to about 9.5 Å. In some embodiments, the distance between the center of the first hydrophobic moiety C and the center of the second hydrophobic moiety D is about 8.0 to about 16.0 Å. In some embodiments, the distance between the center of the first plane to the center of the first hydrophobic moiety C is about 3.0 to about 5.0 Å. In some embodiments, the distance between the center of the second plane to the center of the second hydrophobic moiety C is about 3.0 to about 5.0 Å. In some embodiments, the distance between the center of the first plane to the center of the positive ionizable substituent is about 6.5 to about 9.5 Å.

17 Claims, 10 Drawing Sheets

SMALL MOLECULES AND A PHARMACOPHORE MODEL FOR INHIBITION OF BOTULINUM TOXIN AND METHODS OF MAKING AND USING THEREOF

CROSS REFERENCE TO RELATED APPLICATIONS

This application claims the benefit of U.S. Provisional Patent Application No. 60/501,243, filed 8 Sep. 2003, listing Sina Bavari and James J. Schmidt, as joint inventors, which is herein incorporated by reference in its entirety.

ACKNOWLEDGMENT OF GOVERNMENT SUPPORT

This invention was made by employees of the United States Army. The government has rights in the invention.

BACKGROUND OF THE INVENTION

1. Field of the Invention

The present invention generally relates to inhibitors of Botulinum neurotoxin A metalloprotease activity.

2. Description of the Related Art

Botulinum neurotoxins (BoNTs) are produced by spore forming anaerobic bacteria *Clostridium botulinum*, and are among the most lethal of biological poisons. See Schmidt & Stafford (2003) Appl. Environ. Microbiol. 69:297-303; and Kessler & Benecke (1997) Neurotoxicology 18:761-770. Seven immunologically distinct BoNT serotypes (designated A-G) have been identified. See Simpson, L. L. (1989) BOTULINUM NEUROTOXIN AND TETANUS TOXIN, Academic Press, New York. Accidental exposure to BoNTs, for example, through contaminated food, can result in life threatening flaccid paralysis. See Shapiro, et al. (1998) Ann. Intern. Med. 129:221-228. Furthermore, BoNTs have been weaponized in highly toxic aerosol form, and consequently pose a significant threat to both to civilian and military populations. See Franz, et al. (1997) JAMA 278:399-411; and Arnon, et al. (2001) JAMA 285:1059-1070. As a result, there is an urgent need for therapeutic countermeasures against BoNTs. See Goodnough, et al. (2002) FEBS Lett. 513:163-168.

BoNT is secreted as a holotoxin composed of two peptide chains that are linked by a disulfide bridge. See Lacy & Stevens (1999) J. Mol. Biol. 291:1091-1104. The heavy chain is responsible for: (1) targeting and binding to surface receptors on nerve terminals; (2) translocation into the neuronal cytosol via the formation of a low pH endosome; and (3) protecting the substrate binding cleft of the light chain prior to neuronal internalization. See Turton, et al. (2002) Trends Biochem. Sci. 27:552-558; and Singh, B. R. (2000) Nat. Struct. Biol. 7 (2000) 617-619. The light chain, which dissociates from the heavy chain in the low endosomal pH, is released into the cytosol where it acts as a zinc metalloprotease that cleaves soluble NSF-attachment protein receptor (SNARE) proteins: synaptosomal-associated protein of 25 kDa (SNAP-25), synaptobrevin, and syntaxin. BoNT serotypes A, C, and E cleave SNAP-25; serotypes B, D, F, and G cleave synaptobrevin; and serotype C can also use syntaxin as substrate. See Binz, et al. (1994) J. Biol. Chem. 269:1617-1620; Schiavo, et al. (1992) Nature 359:832-835; Schiavo, et al. (1993a) J. Biol. Chem. 268:23784-23787; Schiavo, et al. (1993c) J. Biol. Chem. 268:11516-1151915; Schiavo, et al. (1993b) J. Biol. Chem. 269:20213-20216; and Blasi, et al. (1993b) EMBO J. 12:4821-4828. Without functional SNARE complexes, acetylcholine is not released into neuromuscular junctions, thereby leading to paralysis.

Research to identify peptide and small molecule inhibitors of BoNT serotype A (BoNT/A) has targeted both holotoxin translocation and light chain (BoNT/A LC) metalloprotease activity. Sheridan et al. and Deshpande et al. have shown that a number of antimalarial agents interfere with BoNT/A translocation into nerve cytoplasm. See Sheridan, et al. (1997) Toxicon 35:1439-1451; and Deshpande, et al. (1997) Toxicon 35:433-445.

Specifically, it has been shown that several antimalarial compounds act subsequent to toxin binding to cell-surface receptors, and it has been hypothesized that these agents inhibit BoNT/A cytosol entry by raising endosomal pH (an endosomal pH of 5.5 or lower is needed for release into the cytoplasm). Hayden et al. have found that BoNT/A LC is inhibited by mM concentrations of known protease inhibitors: captopril, lysinopril, and enalapril. See Hayden, et al. (2003) J. Appl. Toxicol. 23:1-7. In the same study, it was also reported that a number of short peptides, from specific "hinge" libraries, inhibit BoNT/A LC activity by as much as 51% at concentrations as low as 0.5 µM. Using a chromatographic method, Schmidt et al. identified the peptide motif CRATKML as a potent inhibitor. See Schmidt, et al. (1998) FEBS Lett. 435:61-64. In a subsequent study, the Cys residue of CRATKML was replaced with thiol containing organic moieties, and it was found that a 2-mercapto-3-phenylpropionly containing derivative was the most effective (Ki=0.3 µM). See Schmidt & Stafford (2002) FEBS Lett. 532:423-426.

Unfortunately, no small molecule (non-peptidic) inhibitors of BoNT/A LC metalloprotease activity, which are effective in the low µM range, have been reported.

Thus, a need exists for inhibitors of BoNT/A LC metalloprotease activity.

SUMMARY OF THE INVENTION

The present invention generally relates to compounds and pharmacophore models that inhibit BoNT/A LC metalloprotease activity.

In some embodiments, the present invention provides a pharmacophore model for inhibiting Botulinum neurotoxin A metalloprotease activity which comprises a first plane A, a second plane B, a first hydrophobic moiety C, a second hydrophobic moiety D and a positive ionizable substituent E. The pharmacophore model may further comprise a heteroatom in the first plane A. In some embodiments, the distance between the center of the first plane A and the center of the second plane B is about 6.5 to about 9.5 Å. In some embodiments, the distance between the center of the first hydrophobic moiety C and the center of the second hydrophobic moiety D is about 8.0 to about 16.0 Å. In some embodiments, the distance between the center of the first plane to the center of the first hydrophobic moiety C is about 3.0 to about 5.0 Å. In some embodiments, the distance between the center of the second plane to the center of the second hydrophobic moiety C is about 3.0 to about 5.0 Å. In some embodiments, the distance between the center of the first plane to the center of the positive ionizable substituent is about 6.5 to about 9.5 Å. In some embodiments, one or both of the planes comprise a biaryl group or a triaryl group. In some preferred embodiments, the biaryl group is selected from the group consisting of naphthalene, quinoline, isoquinoline, benzofuran, indole, quinazoline, quinoxaline, naphthyridine, phthalazine, and purine. In some preferred embodiments, the triacyl group is selected from the group consisting of acridine, phenazine, phenanthroline, phenanthridine, and carbazole. In some embodiments, the hydrophobic moieties are capable of occupying the binding subsites 1 and 2 of the BoNT/A LC substrate binding cleft. In some preferred embodiments, the hydrophobic moieties are each independently selected from the group consisting of an alkyl group, bromo, chloro, iodo, alkyoxy, and an unsaturated heterocycle. In some embodiments, the positive ionizable substitutent is selected from the group consisting of a carboxylate, a primary amine, a secondary amine, a tertiary amine, a hydroxyl moiety attached to an aromatic ring.

In some embodiments, the present invention provides a method of inhibiting Botulinum neurotoxin A metalloprotease activity which comprises contacting a compound fitting the pharmacophore model provided herein with Botulinum neurotoxin A metalloprotease. In some embodiments, the compound is a bisquinoline. In some preferred embodiments, the compound is selected from the group consisting of Michellamine B; NSC 357756; NSC 119889; NSC 86372; NSC 130796; NSC 402959; Q1-3; Q1-19; Q1-21; Q2-11; Q2-15; Q2-43; Q2-59; Q2-61; Q2-97; Q3-53; Q3-81; and Q3-87.

In some embodiments, the present invention provides a composition comprising a compound fitting the pharmacophore model provided herein. In some embodiments, the compound is a bisquinoline. In some preferred embodiments, the compound is selected from the group consisting of Michellamine B; NSC 357756; NSC 119889; NSC 86372; NSC 130796; NSC 402959; Q1-3; Q1-19; Q1-21; Q2-11; Q2-15; Q2-43; Q2-59; Q2-61; Q2-97; Q3-53; Q3-81; and Q3-87. In some embodiments, the composition further comprises a pharmaceutically acceptable carrier. In some embodiments, the composition further comprises at least one supplementary active compound.

In some embodiments, the present invention provides a method of screening a database of compounds for identifying at least one candidate compound that may inhibit Botulinum neurotoxin A metalloprotease activity which comprises mapping the compounds to the pharmacophore model provided herein.

In some embodiments, the present invention provides a kit comprising at least one compound fitting the pharmcophore model provided herein.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DESCRIPTION OF THE DRAWINGS

This invention is further understood by reference to the drawings wherein.

Red indicates structural components marked for removal; blue indicates added structural components that are predicted to enhance binding.

Figure 7:
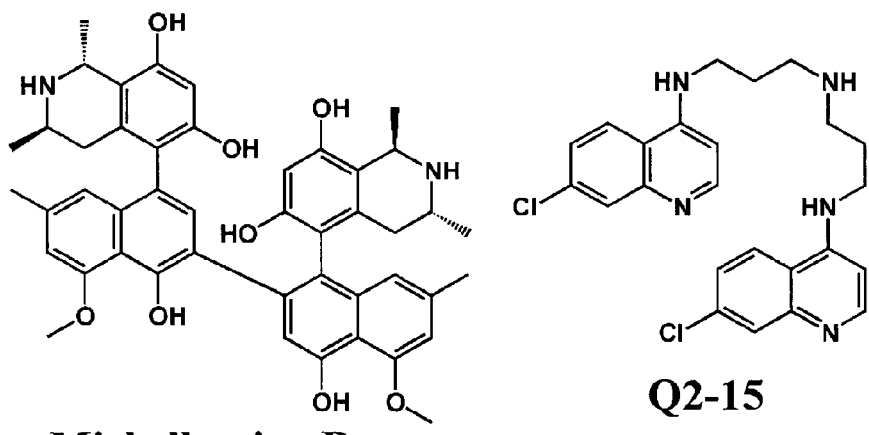

FIG. 7 shows two-dimensional structures of BoNT/A LC metalloprotease inhibitors michellamine B and Q2-15. Michellamine B potency: 62% inhibition at 20 µM conc.; Q2-15 potency: 60% inhibition at 20 µM conc.

FIG. 8 shows comparisons of BoNT/A LC models.

Figure 8A:

FIG. 8A shows all backbone atoms superimposition of the BoNT/A LCs from X-ray crystal structures PDB refcodes=3BTA (red) and 1E1H (blue) as shown in the corresponding figures of Burnett, et al. (2005) Bioorg. Med. Chem. 13:333-341.

Figure 8B:
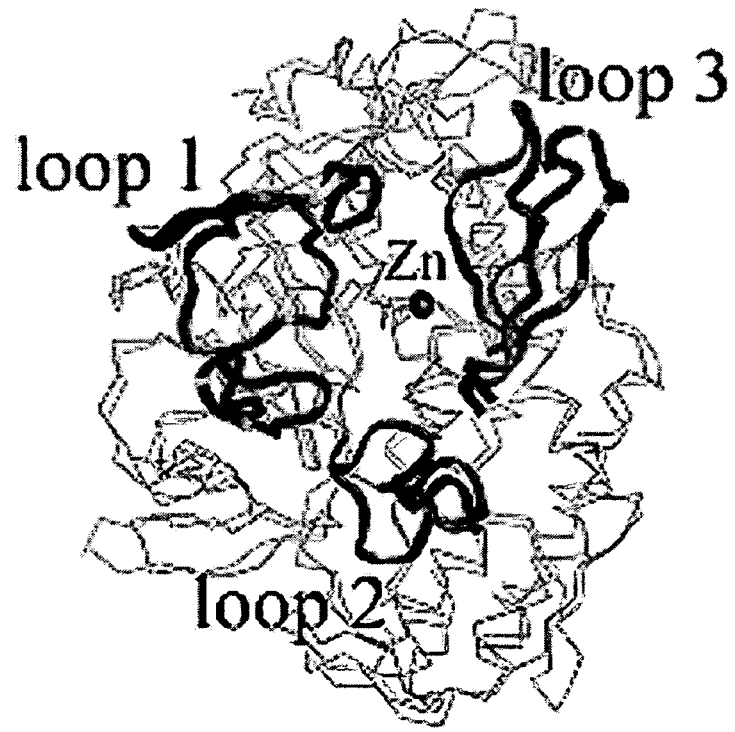

FIG. 8B shows all backbone atoms superimposition of the 3BTA BoNT/A LC X-ray crystal structure (green) and its dynamics average structure (magenta). Loops 1-3 are shown as ribbons as shown in the corresponding figures of (2005) Bioorg. Med. Chem. 13:333-341.

Figure 8C:
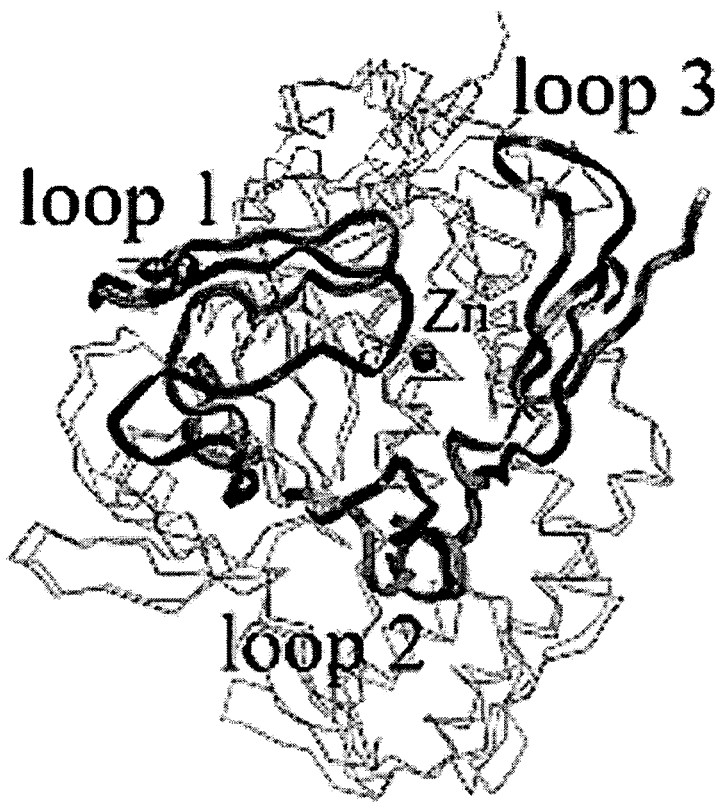

FIG. 8C shows all backbone atoms superimposition of the 1E1H BoNT/A LC X-ray crystal structure (green) and its dynamics average structure (magenta) as shown in the corresponding figures of Burnett, et al. (2005) Bioorg. Med. Chem. 13:333-341. Loops 1-3 are shown as ribbons.

Figure 9A:
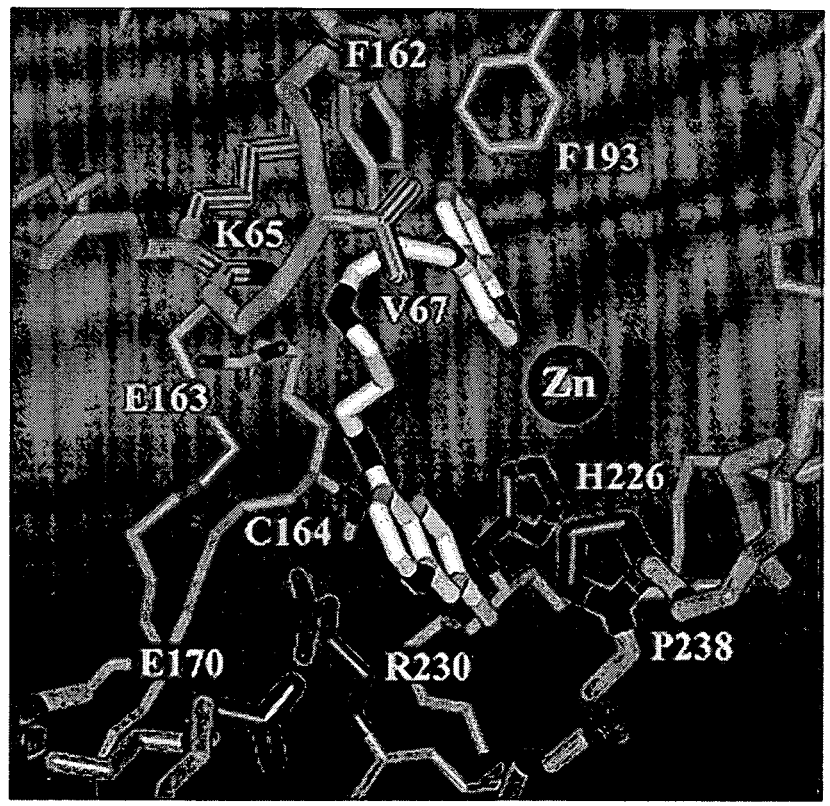

FIG. 9A shows BoNT/A LC inhibitor Q2-15 docked in the molecular dynamics model for the 1E1H BoNT/A LC. In the corresponding figures of (2005) Bioorg. Med. Chem. 13:333-341: Q2-15 carbons are white. Enzyme atom colors: subsite 1 carbons (light blue); subsite 2 carbons (magenta); polar contact region carbons (orange); all other carbons (light green); oxygen (red); nitrogen (blue); sulfur (yellow). Q2-15 carbons are white and chlorine atoms are light green. BoNT/A LC loops 1, 2, and 3, as well as the side-chains of specified residues of these loops are shown in thicker stick. Residues with brown stripes are new contacts that are observed when docking Q2-15 in the dynamics BoNT/A LC (as opposed to contacts made by Q2-15 docked in the molecular mechanics refined X-ray structure).

Figure 9B:
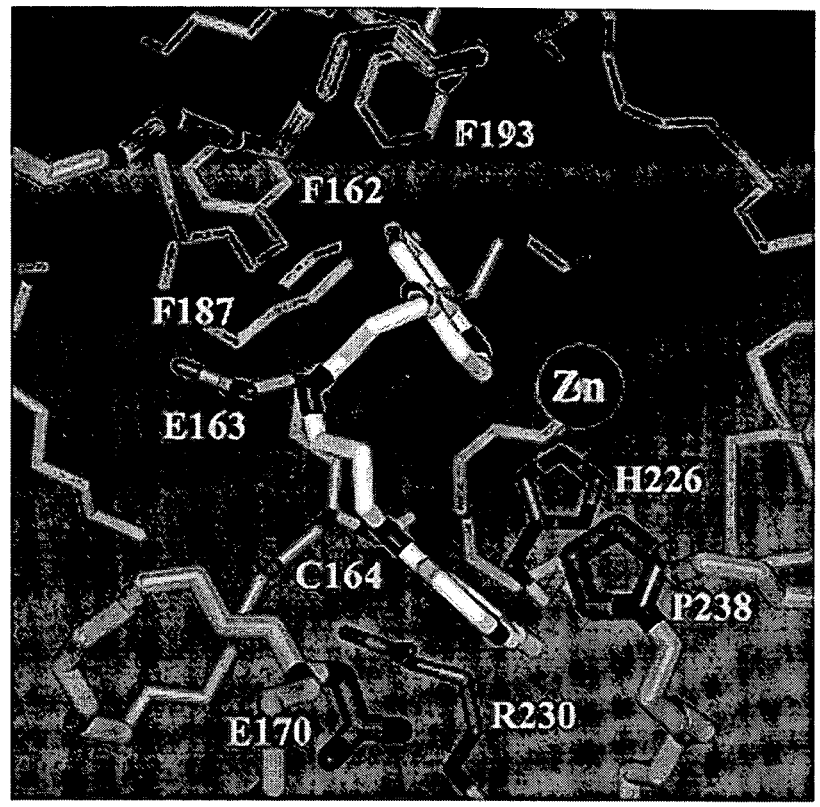

FIG. 9B shows BoNT/A LC inhibitor Q2-15 docked in the molecular mechanics refined X-ray crystal structure of the 1E1H BoNT/A LC. In the corresponding figures of Burnett, et al. (2005) Bioorg. Med. Chem. 13:333-341: Q2-15 carbons are white. Enzyme atom colors: subsite 1 carbons (light blue); subsite 2 carbons (magenta); polar contact region carbons (orange); all other carbons (light green); oxygen (red); nitrogen (blue); sulfur (yellow). Q2-15 carbons are white and chlorine atoms are light green. BoNT/A LC loops 1, 2, and 3, as well as the side-chains of specified residues of these loops are shown in thicker stick. Residues with brown stripes are new contacts that are observed when docking Q2-15 in the dynamics BoNT/A LC (as opposed to contacts made by Q2-15 docked in the molecular mechanics refined X-ray structure). A comparison of FIG. 9A and FIG. 9B shows how loop 1 reorientation provides additional contacts for the inhibitor.

Figure 10A:
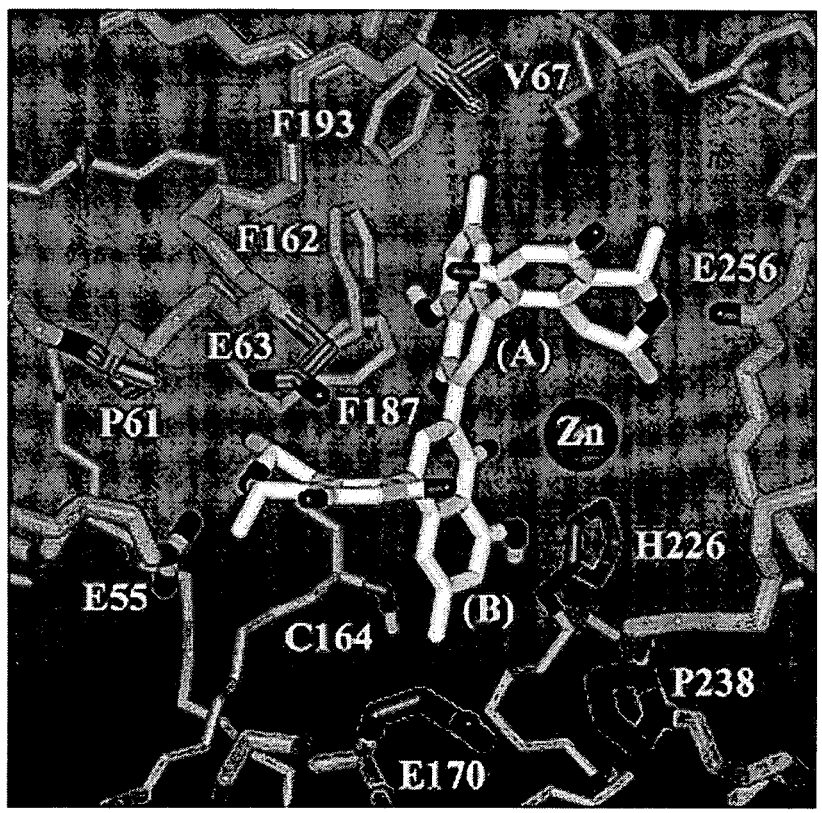

FIG. 10A shows Michellamine B docked in the molecular dynamics structure for the 3BTA BoNT/A LC. In the corresponding figures of Burnett, et al. (2005) Bioorg. Med. Chem. 13:333-341: Michellamine B carbons are white. Enzyme atom colors: subsite 1 carbons (light blue); subsite 2 carbons (magenta); polar contact region carbons (orange); all other carbons (light green); oxygen (red); nitrogen (blue); sulfur (yellow). Q2-15 carbons are white and chlorine atoms are light green. BoNT/A LC loops 1, 2, and 3, as well as the side-chains of specified residues of these loops are shown in thicker stick.

Figure 10B:
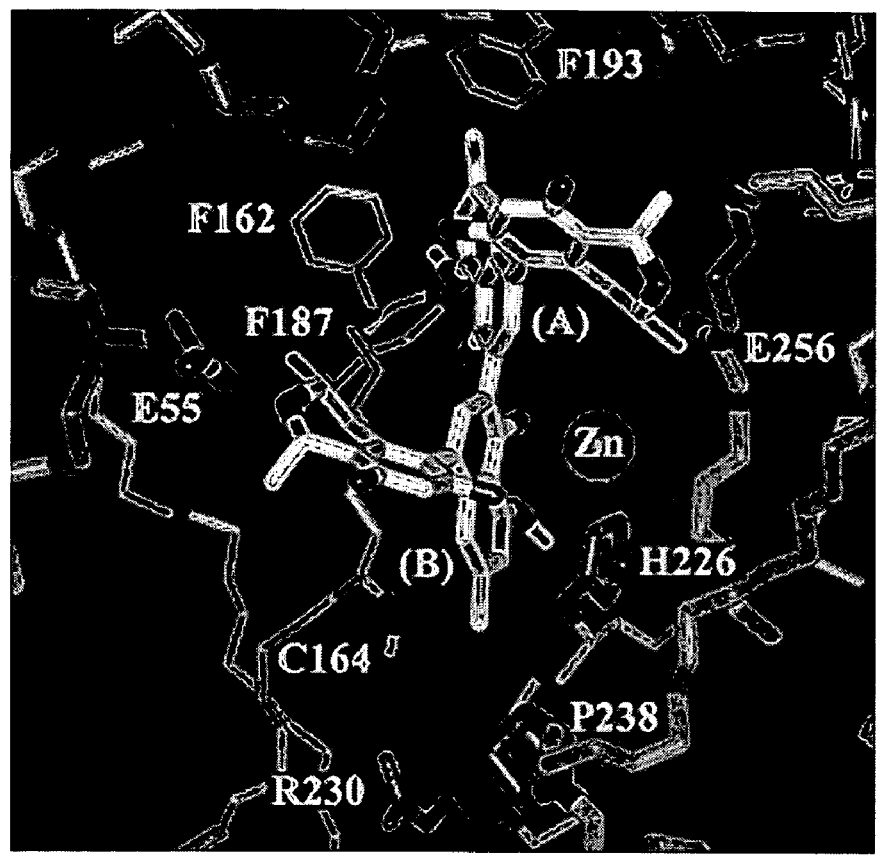

FIG. 10B shows Michellamine B docked in the molecular mechanics refined X-ray crystal structure of the 3BTA BoNT/A LC. In the corresponding figures of Burnett, et al. (2005) Bioorg. Med. Chem. 13:333-341: Michellamine B carbons are white. Enzyme atom colors: subsite 1 carbons (light blue); subsite 2 carbons (magenta); polar contact region carbons (orange); all other carbons (light green); oxygen (red); nitrogen (blue); sulfur (yellow). Michellamine B carbons are white. BoNT/A LC loops 1, 2, and 3, as well as the side-chains of specified residues of these loops are shown in thicker stick. A comparison of FIG. 10A and FIG. 10B shows that their are more favorable electrostatic and hydrophobic contacts between michellamine B and the BoNT/A LC dynamics structure, and that these interactions are the result of loop reorientations toward the substrate binding cleft.

Figure 11:
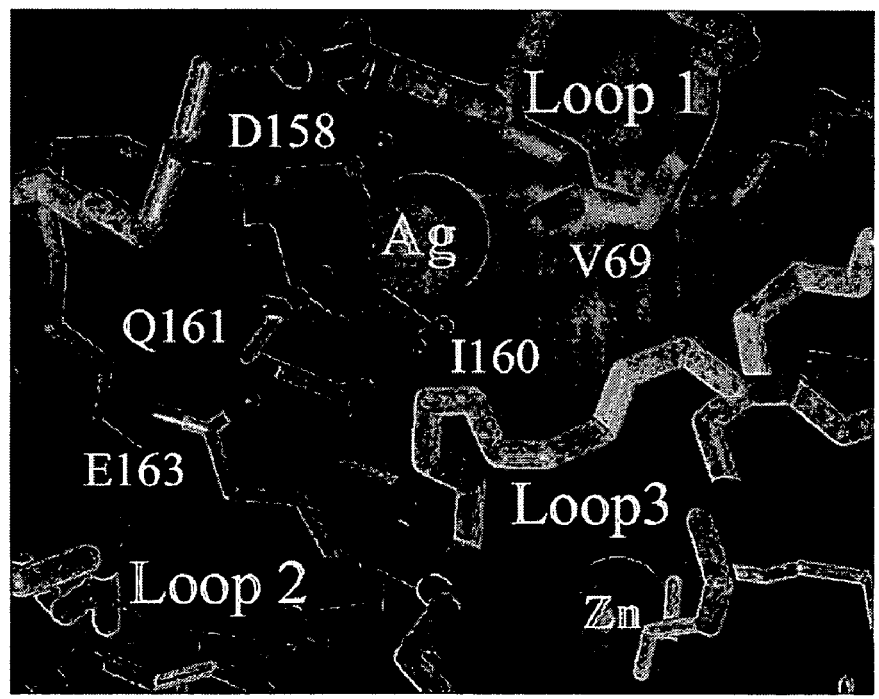

FIG. 11 shows a proposed binding site for silver ion in the dynamics structure of the 3BTA BoNT/A LC. In the corresponding figures of Burnett, et al. (2005) Bioorg. Med. Chem. 13:333-341: Oxygen atoms are red and nitrogen atoms are blue. The silver ion is shown as a light blue sphere and the zinc ion is a magenta sphere. All other atoms are green. Loops 1, 2, and 3 are shown in thicker stick. Loop 1 reorientation partially shields the polar contact region from solvent, creating a pocket that may potentially trap a silver ion.

Figure 12:
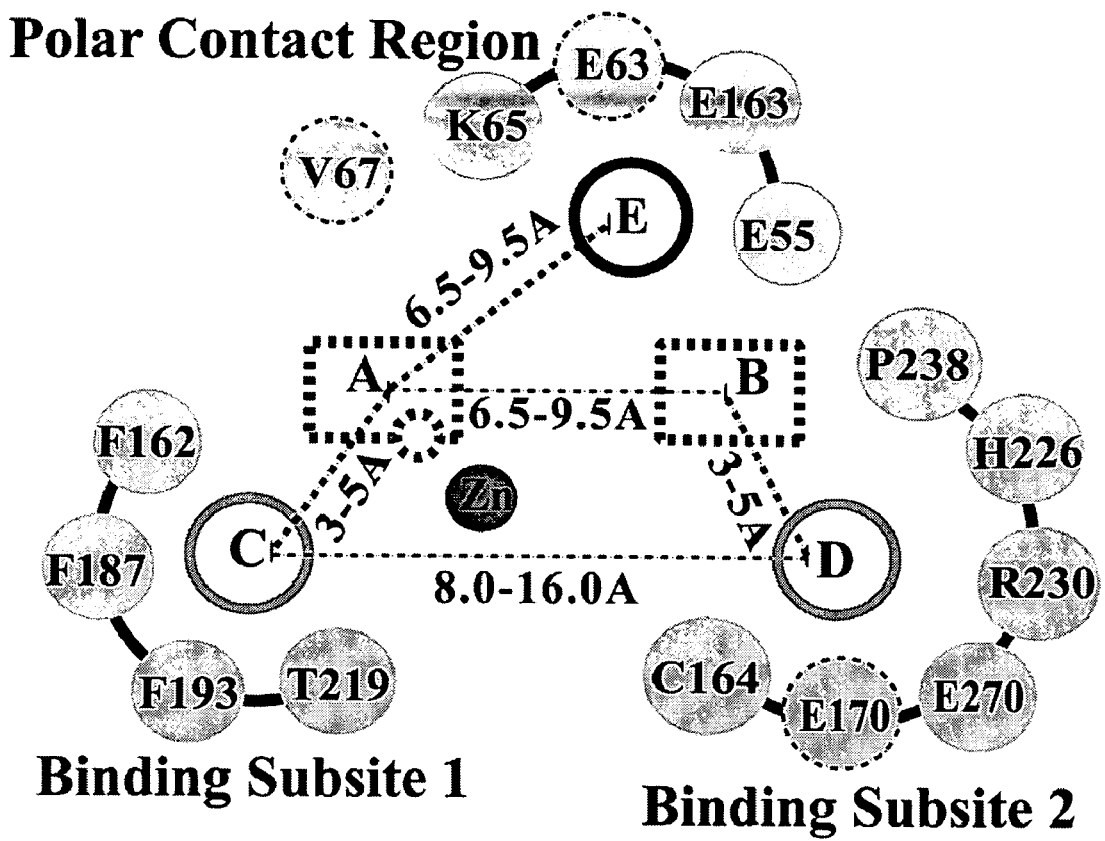

FIG. 12 shows refined pharmacophore for BoNT/A LC inhibition. In the corresponding figures of Burnett, et al. (2005) Bioorg. Med. Chem. 13:333-341: Planar components A and B are blue dashed rectangles. The dashed circle in plane A represents a heteroatom. Hydrophobic components C and D are shown as light blue circles. The positive ionizable component E of the pharmacophore is shown as a red circle. Residues that remained consistent when docking inhibitors in predicted binding subsites of both dynamics and molecular mechanics only refined models are shown as gray spheres. Residues E63, V67 and E170 are shown as a gray spheres with dashed black boarders —to indicate that these amino acids were found to participate when docking inhibitors in dynamics structures.

The color figures are the same as those provided in Burnett, et al. (2003) Biochem. Biophys. Res. Comm. 310:84-93; and Burnett, et al. (2004) Bioorg. Med. Chem., in press, published as Burnett, et al. (2005) Bioorg. Med. Chem. 13:333-341, which are herein incorporated by reference.

DETAILED DESCRIPTION OF THE INVENTION

Botulinum neurotoxins (BoNTs) are among the most lethal biological substances to have been weaponized, and are listed as biodefense category A agents. Currently, no small molecule (non-peptidic) therapeutics exist to counter this threat; hence, identifying and developing compounds that inhibit BoNTs is a high priority. As disclosed herein, a high throughput assay was used to identify small molecules that inhibit the metalloprotease activity of BoNT serotype A light chain (BoNT/A LC). All inhibitors were further verified using a HPLC based assay. Conformational analyses of these compounds, in conjunction with molecular docking studies, were used to predict structural features that contribute to inhibitor binding and potency.

The present invention provides a pharmacophore model for BoNT/A LC inhibitors. In preferred embodiments, the small molecules (non-peptidics) that fall within the pharmacophore model of the present invention inhibit BoNT/A LC metalloprotease activity in low µM range amounts.

As disclosed herein, a high-throughput assay known in the art was used to facilitate BoNT/A LC inhibitor identification. See Schmidt, et al. (2001) Anal. Biochem. 296:130-137. Initially, the National Cancer Institute (NCI) Diversity Set was screened, and several compounds possessing greater than about 50% inhibition (at 20 μM concentration) were identified. Based on molecular modeling studies, common structural features and binding modes in the BoNT/A LC substrate binding cleft were identified for further evaluation. Additional screening of 7-chloro-4-aminoquinoline derivatives also resulted in the identification of candidate compounds that substantially inhibit BoNT/A LC at 20 μM concentrations. Analyses of these compounds indicate that they share common structural/functional group characteristics with inhibitors identified during the screen of the NCI Diversity Set, and that they may also bind to the enzyme's substrate binding cleft in a similar manner. Based on these analyses, the pharmacophore model of the present invention was developed.

As provided in Example 1, a high-throughput fluorescence-based assay was initially used to screen the NCI Diversity Set: a collection of 1990 molecules that were selected to cover a wide range of conformational space, and at the same time provide pharmacophore diversity and structural rigidity. Following the initial high throughput screen, a HPLC based assay was used to eliminate false positives resulting from fluorescence quenching by some of the compounds. The final set of inhibitors, which were tested at 20 μM concentration in the presence 0.1 mM substrate, comprised 21 compounds with potencies ranging from about 14% to about 100% BoNT/A LC inhibition. Two-dimensional structures for compounds possessing greater than about 40% inhibition are shown in Table 1: as follows:

TABLE 1

NCI Diversity Set Inhibitors of BoNT/A LC

| Compound | NSC Number | % Inhibition[1] |
|---|---|---|
| [structure] | 625324 | 100 |
| [structure] | 661755 | 62 |
| [structure] | 357756 | 57 |
| [structure] | 119889 | 56 |

TABLE 1-continued

NCI Diversity Set Inhibitors of BoNT/A LC

| Compound | NSC Number | % Inhibition[1] |
|---|---|---|
| (structure) | 86372 | 51 |
| (structure) | 130796 | 48 |
| (structure) | 402959 | 40 |

[1]Compounds tested in the HPLC based assay at 20 μM conc. In the presence of 0.1 mM substrate.

Additional testing of compound NSC 625324 (silver sulfadiazine), initially the most potent of the identified compounds, indicated that this modecule's efficacy was entirely mediated by the silver ion: no inhibition was observed when the unionized, organic form of sulfadiazine was tested in the HPLC based assay. Furthermore, BoNT/A LC activity was examined in the presence of silver acetate, and 100% inhibition of protease activity was found at concentrations about 5 μM or more silver ion (the $IC_{50}$ was about 1.5 to about 2.0 μM). Cesium and rubidium salts did not inhibit BoNT/A LC protease activity at concentrations up to 20 μM. The presence of zinc (about 5 to about 50 μM) in assays had no effect on inhibition by 3 μM silver ion, but addition of 1 mM DTT immediately reversed inhibition. These observations suggest that silver neither displaces zinc from the active site, nor causes irreversible denaturation by reacting with a residue important for conformational stability. Thus, this ion might bind to polar residues in or near the substrate binding cleft, blocking access to the catalytic site.

Compounds NSC 86372 and 130796 both contain an 8-hydroxyquinoline moiety (Table 1), which is known to chelate metal ions. See Kom, et al. (1999) J. Braz. Chem. Soc. 10:46-50, which is herein incorporated by reference. Both of these molecules do chelate the BoNT/A LC catalytic zinc. Support for a chelation mechanism is based on: (1) assay data showing that several congeners of NSC 86372 possess equivalent inhibitory potency to that of the original lead molecule; (2) addition of 20 μM zinc immediately and quantitatively reversed inhibition caused by up to about 10 μM NSC 86372; and (3) NSC 86372, its congeners, and NSC 130796, inhibit other zinc metalloproteases (including anthrax lethal factor and BoNT serotype B light chain (BoNT/B LC)). Consequently, the 8-hydroxyquinoline motif was deemed to be unsuitable for further development as a component of BoNT/A LC inhibitors; however, as provided herein, structural similarities between NSC 86372 and other identified compounds fit the pharmacophore model of the present invention for BoNT/A LC inhibition.

Congeneric series of N,N-bis(7-chloroquinolin-4yl)alkanediamines and N,N-bis(7-chloroquinolin-4-yl)heteroalkanediamines (collectively referred to as BQs herein) were examined for BoNT/A LC inhibition See Vennerstrom, et al. (1992) J. Med. Chem. 35:2129-2137; and Vennerstrom, et al. (1998) J. Med. Chem. 41:4360-4364, which are herein incorporated by reference. The compounds were tested in the HPLC based assay at 20 μM concentration in the presence of 0.1 mM substrate using methods known in the art. Inhibition of BoNT/A LC by these compounds was not affected by added zinc. Furthermore, when tested against BoNT/B LC protease activity, no significant inhibition was found. Thus, these compounds appear to exhibit specificity for binding to BoNT/A LC, and are not zinc chelators. Table 2 shows the two-dimensional structures of these compounds, along with percent inhibition of BoNT/A LC.

TABLE 2

| Quinoline Based Inhibitors of NoNT/A LC | | |
|---|---|---|
| Compound | NSC Number | % Inhibition[1] |
| Bisquinolines (BQs) | R = Cl  | |
| 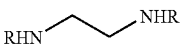  | Q1-21 | 24 |
| 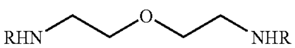  | Q3-87 | 7 |
| 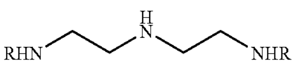  | Q2-59 | 26 |
| 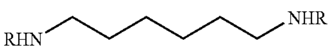  | Q1-19 | 5 |
| 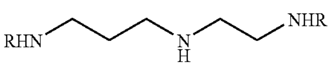  | Q2-61 | 50 |
| 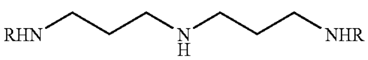  | Q2-15 | 60 |
| 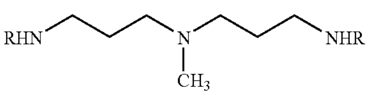  | Q2-43 | 52 |
| 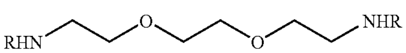  | Q1-3 | 12 |
| 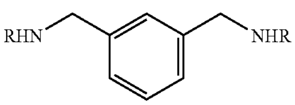  | Q3-81 | 32 |
| 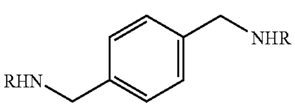  | Q3-53 | 27 |
| 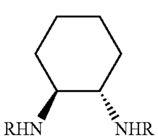  | Q2-97 | 15 |
| 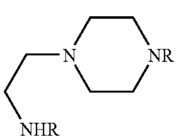  | Q2-11 | 8 |
| Antimalarial Drugs | | |
| 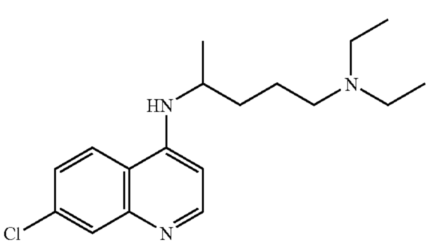  | Chloroquine (racemic) | 20 |

TABLE 2-continued

Quinoline Based Inhibitors of NoNT/A LC

| Compound | NSC Number | % Inhibition[1] |
|---|---|---|
| Bisquinolines (BQs) R=Cl (quinoline structure) | | |
| Quinacrine (racemic) | | 30 |
| Amodiaquine | | 20 |
| Quinine (* = r) | | 9 |
| Quinidine (* = r) | | 3 |

[1]Compounds tested in the HPLC based assay at 20 μM conc. In the presence of 0.1 mM substrate.

Results from the studies on BQs led to the hypothesis that other quinoline based compounds might also inhibit BoNT/A LC enzymatic activity. One method for fast tracking the evolution of therapeutics against BoNT/A LC is to identify inhibitors of this enzyme that are already approved drugs (and subsequently already possess pharmacological and toxicological data from clinical trials). Subsequently, five readily available antimalarial drugs, amodiaquine, chloroquine, quinacrine, quinidine, and quinine, that share similar structural characteristics with the BQs were tested. These compounds were obtained and examined in the HPLC based assay. The structures of these compounds and percent inhibition of BoNT/A LC protease activity are shown in Table 2.

Figure 1:
FIG. 1 shows an overlay of BoNT/A LC inhibitors from the NCI Diversity Set. For all structures, nitrogen atoms are blue, oxygen atoms are red, and iodine atoms are orange. In the corresponding figures of Burnett, et al. (2003) Biochem. Biophys. Res. Comm. 310:84-93: Carbon atoms for Michellamine B are green, for NSC 86372 are light blue, for NSC 357756 are magenta, and for NSC 119889 are white. There are structural trends in: (1) the superimposed aromatic scaffolds; and (2) the positioning of hydrophobic moieties.

Superimpositions of several of the most potent inhibitors identified during the NCI Diversity Set screen are shown in FIG. 1. An evident feature to emerge from superimposing these compounds is that they all possess biaryl and triaryl heterocyclic scaffolds/groups, for example, quinoline, phenazinium, xanthene, or the like. The exception to this observation is Michellamine B as the central naphthalenes of this molecule do not possess heteroatoms. However, like aromatic heterocyclic nitrogens or oxygens, hydroxy and methoxy substituents on the naphthalene rings may participate in electron donating interactions. The superimposed structures in FIG. 1 also indicate that possessing hydrophobic moieties at either end of the aromatic components may be important for potency.

To gain a better understanding of how these inhibitors interact with BoNT/A LC, molecular docking studies were performed. Michellamine B (Table 1) was the first inhibitor to be examined. This molecule was the best lead for initially probing the steric constraints of the substrate binding cleft, as it is an atropisomer that results from hindered rotation about single bonds; it possesses restricted conformations, which reduces the number of potential binding modes that it may assume in the enzyme's substrate binding cleft. See Hallock, et al. (1997) J. Nat. Prod. 60:677-68331; Manfredi, et al. (1991) J. Med. Chem. 34:3402-340532; Boyd, et al. (1994) J.

Med. Chem. 37:1740-174533; and Bringmann, et al. (1993) Chem. Int. Ed. Engl. 32:1190-1191, which are herein incorporated by reference. Furthermore, unlike NSC 86372, inhibition of BoNT/A LC by Michellamine B is not affected by added zinc, thereby suggesting that inhibition is not simply the result of Michellamine B acting as a chelator.

Figure 2:
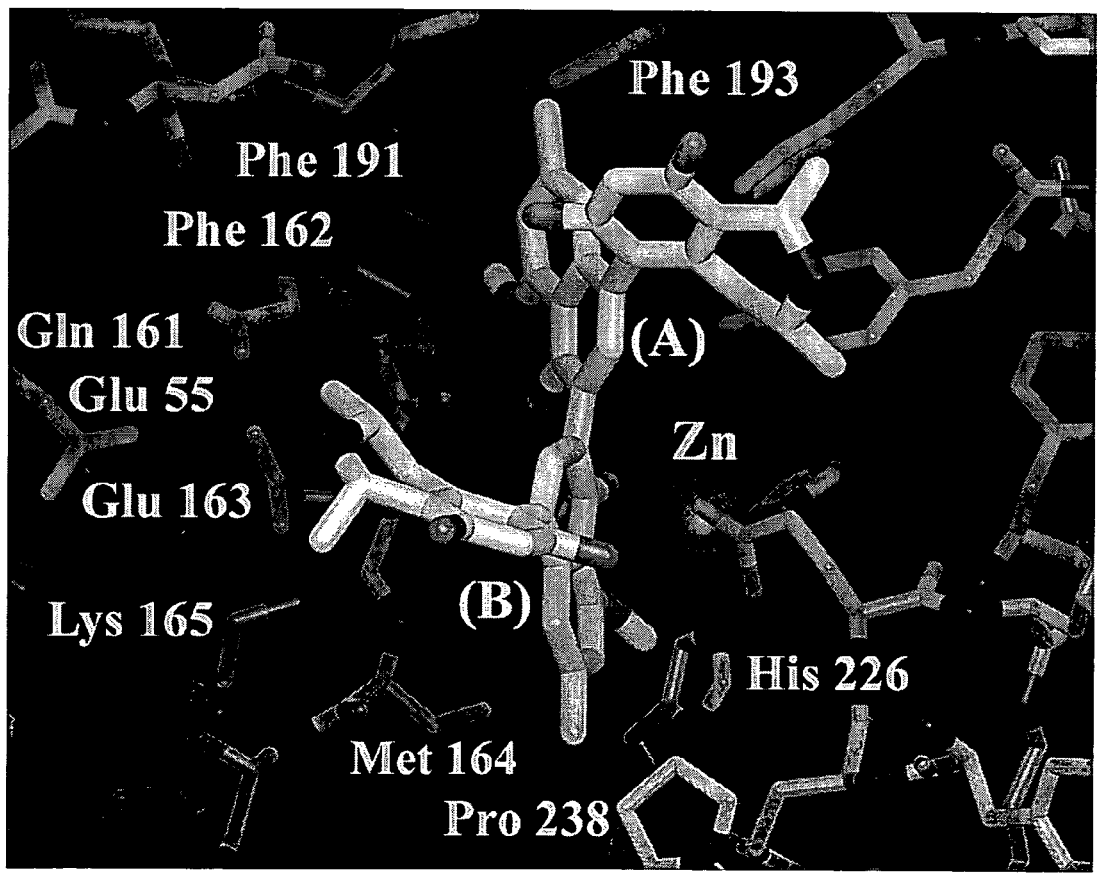
FIG. 2 shows Michellamine B docked in the BoNT/A LC substrate binding cleft. In the corresponding figures of Burnett, et al. (2003) Biochem. Biophys. Res. Comm. 310:84-93: Nitrogen atoms are blue and oxygen atoms are red. Carbon atoms of Michellamine B are white, and the naphthalene scaffolds of the inhibitor are labeled A and B. Carbon atoms of residues in predicted binding subsites are light blue (binding subsite 1), light green (binding subsite 2), and magenta (referred to as the polar region). All other enzyme carbons are green. For Michellamine B, the methoxy and methyl substituents of naphthalene A pack into binding subsite 1, while the methoxy of naphthalene B packs into binding subsite 2. The ionizable nitrogen of the tetrahydroisoquinoline attached to naphthalene B points toward a cluster of polar residues: Glu 55, Gin 161, Glu 163, and Lys 165.

FIG. 2 shows Michellamine B docked in the BoNT/A LC substrate binding cleft. As shown in FIG. 1, there is a good complement between the steric space of the binding cleft and the twist planar conformation of Michellamine B. Hydropathic analyses of favorable and unfavorable contacts in several docked models indicated that the best binding mode results when the naphthalenes (labeled A and B for descriptive purposes) extend down the length of the catalytic cleft. In this model, the two hydroxyl moieties of the naphthalenes exist in close proximity to the catalytic zinc, and form an intramolecular hydrogen bond. Either of the hydroxyl moieties may displace the water molecule that is used by the enzyme's catalytic engine during peptide lysis.

As seen in FIG. 2, the methoxy and methyl groups of naphthalene A point toward a hydrophobic pocket (binding subsite 1) that is formed by the aromatic side-chains of residues Phe 162, Phe 177, and Phe 193, as well as the side-chain methyl of Thr 219. The methoxy moiety of naphthalene B packs into a deep pocket (binding subsite 2) that is located behind His 226 of the catalytic engine, and surrounded by residues Met 164, Thr 175, Arg 230, and Pro 238. The methyl moiety of naphthalene B packs into space behind the side-chain pyrrolidine of Pro 238.

The tetrahydroisoquinoline attached to naphthalene A binds in such a way that the 6,8-diol moieties point toward the solvent, while the 1,3-dimethyl moieties point toward hydrophobic residues of the substrate binding cleft. The ionizable amine of the tetrahydroisoquinoline attached to naphthalene B points towards a cluster of polar residues including Glu 55, Gin 161, Glu 163, Lys 165 and Arg 176, and may either engage directly in an ionic bond with one of the Glu residues in this area, or participate in a water mediated hydrogen bond with any of the indicated polar residues. See FIG. 2. Along the same lines, the ionizable amine may also serve to solubilize the tetrahydroisoquinoline ring. The 6,8-diol substituents of this tetrahydroisoquinoline are oriented toward the solvent interface.

Figure 3:
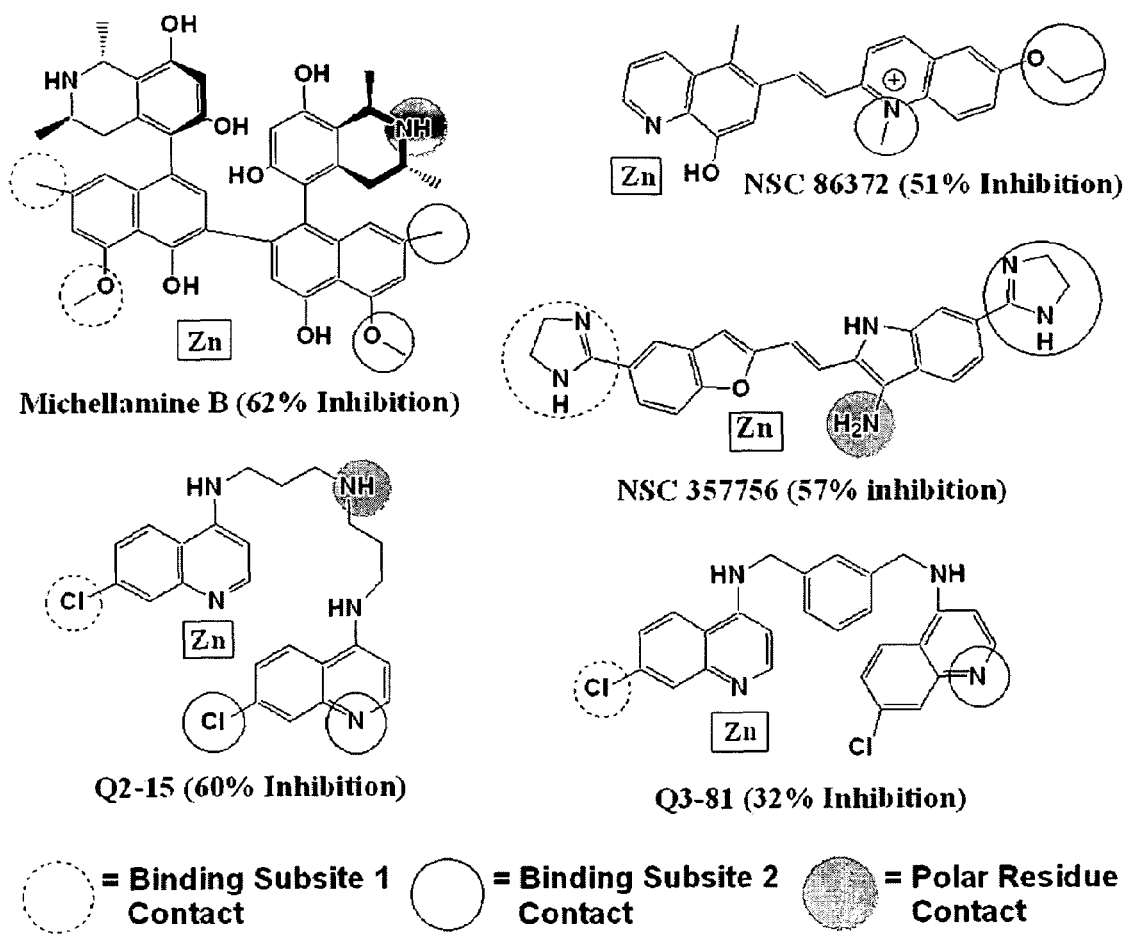
FIG. 3 shows a two-dimensional schematic relating compound substituents to predicted binding subsites in the BoNT/A LC substrate binding cleft. Dashed circles indicate substituents that engage in favorable contacts in binding subsite 1, solid circles indicate substituents that engage in favorable contacts in binding subsite 2, and gray spheres indicate substituents that engage in favorable interactions with polar residues.

Subsequent docking studies with other BoNT/A LC inhibitors from the NCI Diversity Set indicated that these compounds may use binding modes similar to that of Michellamine B. FIG. 3 shows a two-dimensional schematic that matches inhibitor substituents with proposed binding subsites for three inhibitors from the NCI Diversity Set. Analyses indicate that the most potent inhibitors engage in contacts with residues in both binding subsites 1 and 2, and in each case, either an oxygen or a nitrogen (in an aromatic heterocyclic ring) is positioned in close proximity to the catalytic zinc. For example, the 8-hydroxyquinoline of NSC 86372 (FIG. 3), when optimized in the substrate binding cleft, is positioned in such a way that zinc chelation is possible. Additionally, the methyl substituent of the compound's quinolinium substituent inserts into binding subsite 2 (similar to the methoxy moiety of Michellamine B naphthalene B), while the ethoxy moiety of the quinolinium fills space located behind Pro 238 (similar to the methyl moiety of Michellamine B naphthalene B).

In another example, the most favorable binding mode of NSC 357756 indicates that the dihydroimidazolyl (attached to the benzofuran) inserts into binding subsite 1 (FIG. 3) (the same pocket that is occupied by the methoxy and methyl moieties of Michellamine B naphthalene A (FIG. 2)). The oxygen of the benzomran moiety is positioned in close proximity to the zinc ion, and the 3-amino substituent on the indole ring engages in a hydrogen bond with Glu 163. In binding subsite 2, a nitrogen in the dihydroimidazolyl (which is attached to the 6 position of the indole) engages in a hydrogen bond with the side-chain guanidinium of Arg 230, while the methylenes of this ring pack behind the pyrrolidine ring of Pro 238.

BQs possessing a flexible linker between the 7-chloro-4-aminoquinoline moieties were found to be more potent inhibitors than conformationally constrained derivatives (Table 2). In addition, it is also evident that an ionizable amine in the flexible linker increases potency (for example Q2-61 versus Q1-19). Compound Q2-15 shows that a seven atom linker, with a central ionizable amine, is favored over shorter linkers that also contain an ionizable amine.

Figure 4A:
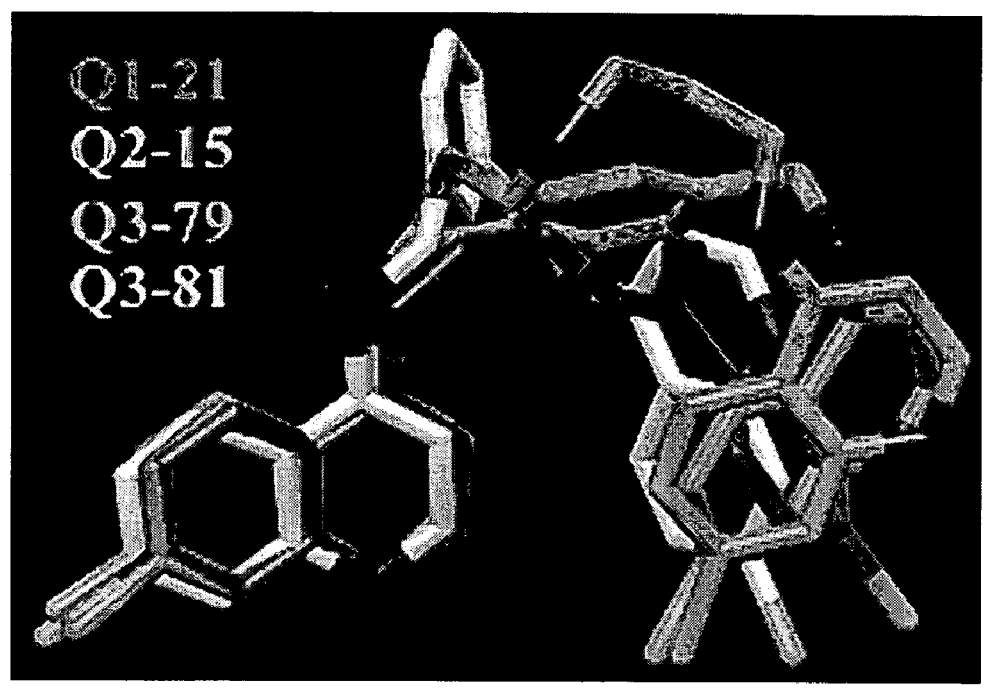
FIG. 4A shows an overlay of folded conformers of BQs: Q1-21, Q2-15, Q3-79, and Q3-81. In the corresponding figures of Burnett, et al. (2003) Biochem. Biophys. Res. Comm. 310:84-93: For all compounds, nitrogen atoms are dark blue and chlorine atoms are light green. The carbon atoms of Q1-21 are magenta, of Q2-15 are light blue, of Q3-79 are green, and of Q3-81 are white. A striking feature of the superimposed compounds is the close correspondence of their chloro substituents, which provides evidence that they may bind within the enzyme's substrate binding cleft in a similar manner.

Conformational analyses of the most potent BQs shows that these compounds favor a folded conformation, with the 7-chloro-4aminoquinoline moieties positioned front to back and slightly offset relative to one another as shown in FIG. 4A. Based on these observations, it appears that these congeners may all bind in the BoNT/A substrate binding cleft in a similar manner.

Figure 4B:
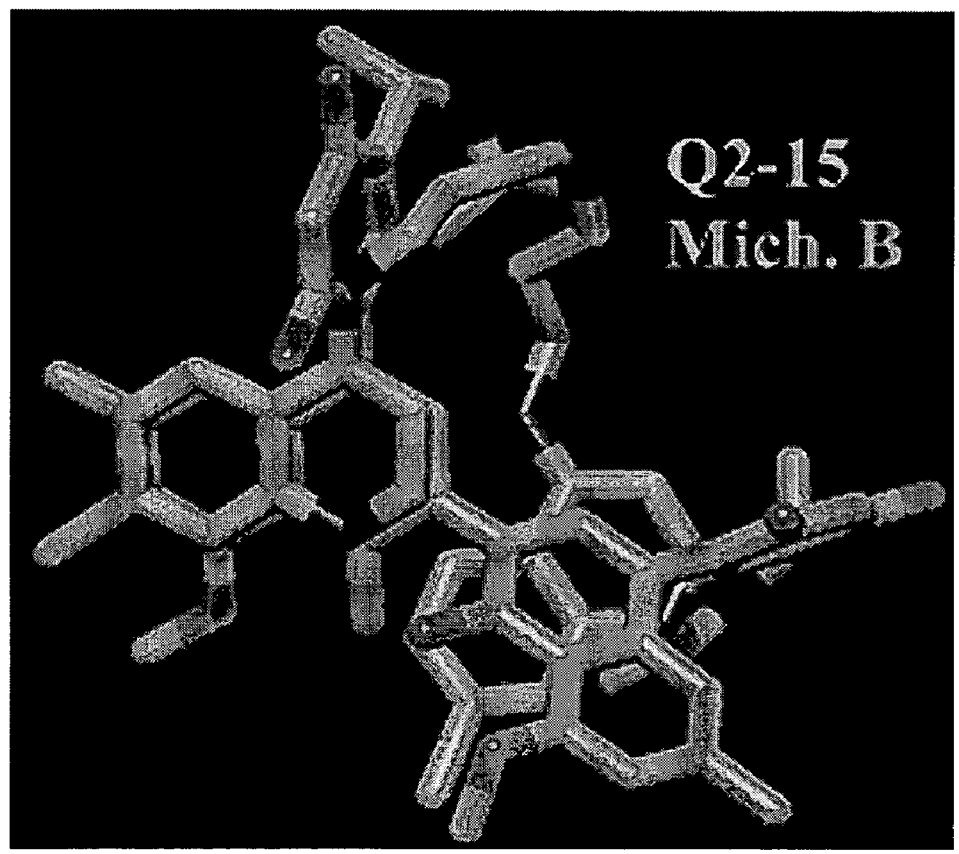
FIG. 4B shows an overlay of Michellamine B and Q2-15. In the corresponding figures of Burnett, et al. (2003) Biochem. Biophys. Res. Comm. 310:84-93: Carbons of Michellamine B are green and carbon atoms of Q2-15 are light blue. The superimposed conformers show a good correspondence between: (1) the ionizable amine in the flexible linker of Q2-15 and the ionizable amine in one of the tetrahydroisoquinolines of Michellamine B; and (2) the chloro moieties of Q2-15 and the hydrophobic methoxy/methyl moieties of Michellamine B.

To gain a better understanding of how the folded conformations of these congeners might bind in the BoNT/A LC substrate cleft, Q2-15 was fit onto Michellamine B (in its docked conformation). The superimposition shown in FIG. 4B indicates a good overlap between: (1) the 7-chloro-4-aminoquinoline components of Q2-15 and the naphthalene moieties of Michellamine B; and (2) the ionizable nitrogen of the Q2-15 flexible linker and the ionizable nitrogen of one of the Michellamine B isoquinolines.

These observations led to docking studies to determine if the BQs might also bind to predicted subsites 1 and 2 in the BoNT/A LC substrate binding cleft. For the most potent compounds, the ring nitrogen of one of the 7-chloro-4-aminoquinoline moieties sits in close proximity to the catalytic zinc, while the 7-chloro substituent packs into binding subsite 1. The ionizable amines in compounds with flexible linkers engage in potential ionic bonds with the polar side-chains of either Gin 161 or Glu 163. Another explanation for the importance of the ionizable amine may be that it is necessary for solubilizing the otherwise hydrophobic linkers found in this series of compounds.

Docking studies also indicate that the second 7-chloro-4-aminoquinoline moiety (of the most potent derivatives) binds in subsite 2 such that the nitrogen of the heterocycle points toward the solvent and engages in a hydrogen bond with the side-chain guanidinium of Arg 230 (as was also observed for a nitrogen in one of the dihydro-imidazolyl rings of NSC 357756), and the 7-chloro substituent points into the hydrophobic space behind His 226. For comparison, molecular docking of compounds with rigid linkers (for example Q2-11, and Q2-97) indicates that steric constraints prevent these compounds from adopting binding modes in subsites 1 and 2 that are as favorable as those observed for congeners with flexible linkers. In general, these studies provide evidence that the BQs interact with the BoNT/A LC substrate binding cleft in a manner similar to inhibitors from the NCI Diversity Set. FIG. 3 shows two-dimensional schematics matching substituents from two of the most potent BQs (Q2-15 and Q3-81) with their corresponding binding subsites in the BoNT/A LC substrate binding cleft.

Of the five examined antimalarial drugs (Table 2), amodiaquine and quinacrine were the most potent (30% inhibition of protease activity). However, the fact that these two drugs inhibit BoNT/A LC with about half the potency of Q2-15 provides further evidence that a second aromatic component, such as found in the BQs or Michellamine B, is necessary for enhanced potency, and supports our hypothesis that binding subsite 2 (in the enzyme's substrate binding cleft) is an important contact region for inhibitors. Furthermore, as quinacrine contains an acridine scaffold, these studies have revealed a new aromatic component that may be used to identify, synthesize new BoNT/A LC inhibitors, or both.

The antimalarial agents found to inhibit BoNT/A LC protease activity have previously been shown to increase the time to BoNT/A holotoxin induced muscle paralysis. See Sheridan, et al. (1997) Toxicon 35:1439-1451; and Deshpande, et al. (1997) Toxicon 35:433-445, which are herein incorporated by reference. In the earlier work, it was hypothesized that these compounds delayed paralysis by interfering with toxin translocation into the nerve cytoplasm, and therefore they were not tested for specific inhibition of BoNT/A LC protease activity. The percent inhibition of BoNT/A LC that was observed for these drugs was not equivalent to the level of protection that they afforded against muscle paralysis in the previous studies. For example, quinacrine, which, as disclosed herein, inhibits BoNT/A LC protease activity by about 30% at 20 μM, was found, in an earlier study, to delay the time to about 50% muscle paralysis by at least about 30% (over control) at 3.3 μM. See Sheridan, et al. (1997) Toxicon 35:1439-1451, which is herein incorporated by reference. Thus, the results from the earlier studies, combined with the findings from our investigation, suggest that these compounds possess a dual mechanism of action—interfering with both BoNT/A entry into the cytoplasm and with the protease activity of the light chain. This dual mechanism of action is appealing from a drug design standpoint, as one molecule can be used to inhibit two separate functions of the same target. Indeed, if the BQs are found to also inhibit BoNT/A cytoplasm entry, then these studies will be the basis for the development of a new family of bifunctional inhibitors.

Figure 5A:
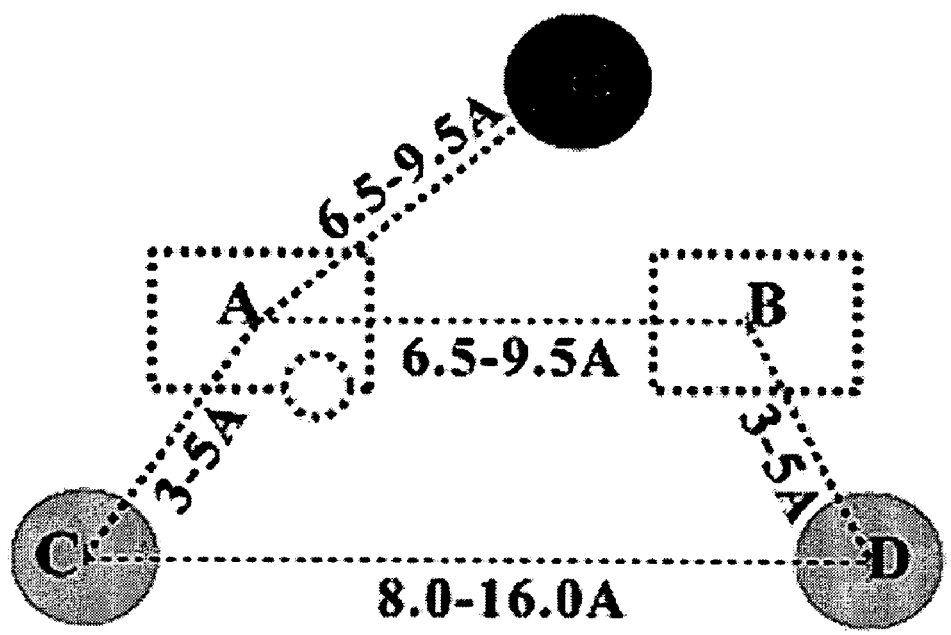
FIG. 5A shows the pharmacophore model of the present invention for BoNT/A LC inhibition. In the corresponding figures of Burnett, et al. (2003) Biochem. Biophys. Res. Comm. 310:84-93: Planar components A and B are blue dashed rectangles. The dashed green circle in plane A represents a heteroatom. Hydrophobic components of the pharmacophore (C and D) are shown with light blue spheres. The positive ionizable component of the pharmacophore (E) is shown with a red sphere.
Figure 5B:
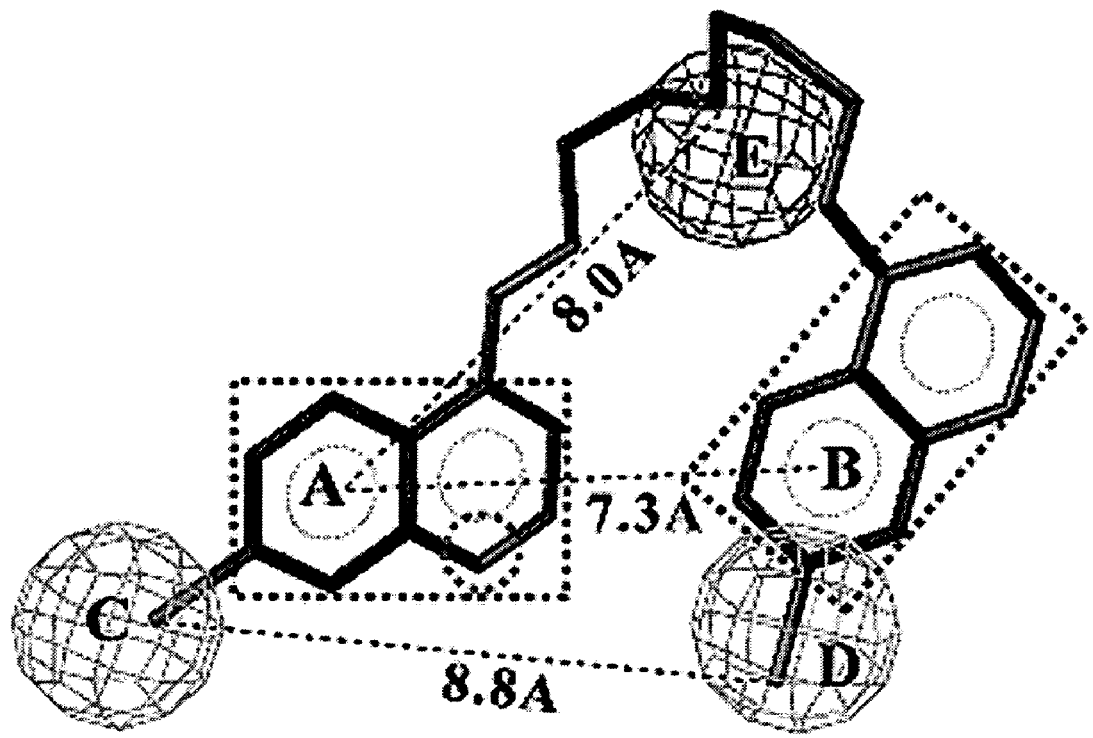
FIG. 5B shows compound Q2-15 mapped onto the pharmacophore (shown in FIG. 5A) in Catalyst 4.7 (Accelrys, Inc. San Diego, Calif.). In the corresponding figures of Burnett, et al. (2003) Biochem. Biophys. Res. Comm. 310:84-93: Carbon atoms are black, nitrogen atoms are blue, and chlorine atoms are green. Planar components A and B are outlined with blue dashed rectangles. The heteroatom in plane A is indicated with a dashed green circle. Mapping of the hydrophobic components (C and D) is indicated with light blue mesh spheres; mapping of the positive ionizable component (E) is indicated with a red mesh sphere.

Based on conformational sampling and molecular docking studies, the present invention provides a pharmacophore model for BoNT/A LC inhibitors as shown in FIG. 5A. An example of how one of the inhibitors (Q2-15) fits the pharmacophore, using Catalyst 4.7 (Accelrys, Inc, San Diego, Calif.) as the query engine, is shown in FIG. 5B. As provided herein, the BoNT/A LC binding cleft can accommodate up to two biaryl/triaryl aromatic components, which are defined by planes A and B in the pharmacophore. See FIG. 5A. These planes serve as scaffolds for positioning other components of the pharmacophore, provided that the distance between centroids of the two planes only varies from about 6.5 to about 9.5 Å. See FIG. 5A. Planes A and B may be in parallel or perpendicular to each other. In some embodiments, a heteroatom is also present in plane A (FIG. 5A) and may serve to either directly engage in an interaction with the catalytic zinc, or replace the water molecule used by zinc during substrate lysis. Examples of structural components of inhibitors that occupy planes A and B include: the two quinoline rings of BQs (a quinoline nitrogen would be the electron donor) (Table 2, FIG. 3, FIG. 4, and FIG. 5B); the two naphthalene rings of Michellamine B (a hydroxyloxygen would be the electron donor) (Table 1, FIG. 2 and FIG. 3); and the indole and benzofuran rings of NSC 357756 (the benzofuran oxygen would be the electron donor) (Table 1 and FIG. 3).

The pharmacophore model of the present invention also includes two hydrophobic moieties (C and D). See FIG. 5A. In relation to the BoNT/A LC substrate binding cleft, C and D correspond to binding subsites 1 and 2, and facilitate hydrophobic collapse between inhibitors and the enzyme. The C→D distance range of the pharmacophore model shown in FIG. 5A reflects the extent of the potential binding space that inhibitors may occupy in subsite 2 of the BoNT/A LC substrate binding cleft. Examples of C and D in inhibitors, as they map to the common pharmacophore, include: the two methoxy substituents of Michellamine B (separated by a distance of 8.6 Å) (Table 1, FIG. 2 and FIG. 3); the two chlorines of the BQs (separated by an average distance of about 9.8 Å for all examined BQs) (Table 2, FIG. 3, FIG. 4, and FIG. 5B); and the two dihydroimidazolyl moieties of NSC 357756 (separated by a distance of about 15.8 Å) (Table 1 and FIG. 3).

The pharmacophore model of the present invention also includes a positive ionizable substituent (E). See FIG. 5A. While inhibitor docking studies have shown that an ionizable moiety may participate in electrostatic interactions with enzyme residues, the positive charge may also aid in solubilizing inhibitors bound within the BoNT/A LC substrate binding cleft; unlike a traditional binding pocket, the BoNT/A LC substrate binding cleft is large, and almost completely solvent exposed. Hence, it is plausible that a hydrogen bonding network involving the positively charged moiety or moieties of the inhibitors and surrounding water molecules also serves to stabilize compound binding. Examples of inhibitor components that map to E include: the ionizable secondary nitrogen in one of the Michellamine B tetrahydroisoquinolines (Table 1, FIG. 2 and FIG. 3); the secondary nitrogens in the flexible linkers of BQs (Table 2, FIG. 3, FIG. 4, and FIG. 5B); and the tertiary nitrogens in amodiaquine, chloroquine, and quinacrine (Table 2). Interestingly, the determined BoNT/A LC peptide cleavage site of the natural substrate, SNAP-25, is between a glutamine and an arginine. See Vaidyanathan, et al. (1999) J. Neurochem. 72:327-337, which is herein incorporated by reference. Furthermore, the distance between the side chain guanidinum of arginine (which is ionized at physiological pH) and the backbone Cα of this residue corresponds to the distance between A and E in the pharmacophore model. Hence, it is possible that the ionizable substituent of the inhibitors may be mimicking contacts made by the side chain guanidinium of the indicated Arg residue of SNAP-25.

Thus, the present invention provides small organic (non-peptidic) compounds that inhibit BoNT/A LC protease activity in the low μM range and a pharmacophore model. This pharmacophore model of the present invention may be used for directing future database mining studies and synthetic organic chemistry projects to identify and develop further BoNT/A LC inhibitors with enhanced potency.

Figure 6:
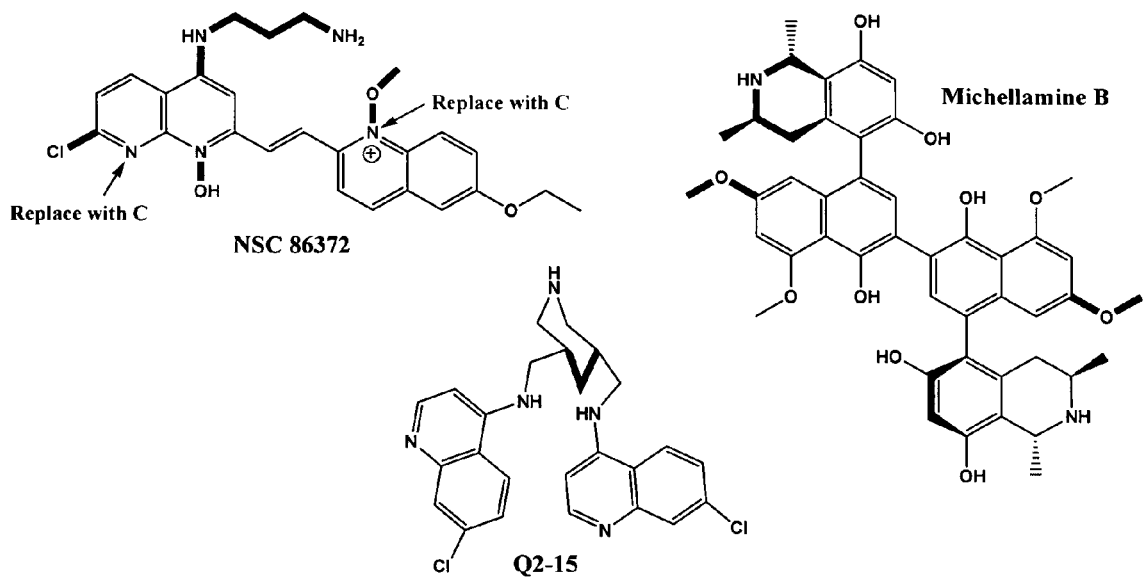
FIG. 6 shows suggested structural/functional group changes for improving the binding of identified inhibitors (Michellamine B, NSC 86372, and Q2-15) in the BoNT/A LC substrate binding cleft. In the corresponding figures of Burnett, et al. (2003) Biochem. Biophys. Res. Comm. 310:84-93.

As shown in FIG. 6, the pharmacophore model of the present invention may be used to modify compounds using methods known in the art in order increase or improve BoNT/A LC inhibition. Examples of structural modifications that may improve BoNT/A LC inhibitory properties of three of the compounds shown in FIG. 6 include: (1) Replacing the 5-methyl-quinolin-8-ol component of NSC 86372 with a 7-chloro-4aminoquinoline would allow for new hydrophobic contacts in binding subsite 1, and would also eliminate non-specific zinc chelation by the 8-hydroxy-quinoline of the original inhibitor. Substituting the 4-amino position with a propylamine side chain would also bring this compound in line with the pharmacophore. Additionally, analyses indicate that the charged nitrogen in the quinolinium ring may be replaced with a carbon, and that the original methyl moiety may be replaced by a methoxy substituent—to enhance hydrophobic contacts in binding subsite; (2) Improving Michellamine B binding involves removing the 1,3 methyl substituents that flank the ionizable amine in one of the tetrahydro-quinolines. This would allow for better potential ionic contacts with the acidic residues in the indicated polar region of the substrate binding cleft, and/or would make this nitrogen more solvent accessible. Additionally, replacing the 6 position methyl moieties of the naphthalene rings with methoxy moieties may enhance contacts in binding subsites 1 and 2; and (3) For Q2-15, conformational analyses have indicated that incorporating a rigid piperidine into the linker locks this compound into a folded conformation, which, based on docking studies, is favorable for binding.

As provided herein, the loop movements and conformational/positional analyses of residues within the substrate binding cleft were studied with respect to BoNT/A LC inhibitor binding and the pharmacophore of the present invention. The X-ray crystal structures of two BoNT/A LCs (PDB reference codes=3BTA and 1E1H) were examined. Results from these analyses indicate that the core structural features of the examined BoNT/A LCs, including α-helices and β-sheets, remained relatively unchanged during 1 ns dynamics trajectories. However, conformational flexibility was observed in surface loops bordering the substrate binding clefts in both examined structures. These analyses indicate that these loops may possess the ability to decrease the solvent accessibility of the substrate binding cleft, while at the same time creating new residue contacts for the inhibitors.

BoNTs are composed of a heavy chain (HC) (100 kDa) and a light chain (LC) (50 kDa), which are linked by a disulfide bridge. See Lacy & Stevens (1999) J. Mol. Biol. 291:1091. The HC is responsible for: (1) binding to surface receptors on cholinergic nerve terminals; (2) plasma membrane penetration via receptor mediated endocytosis; and (3) toxin release into the nerve cytosol. See Turton, K., et al. (2002) Trends. Biochem. Sci. 27:552; Singh, B. R. (2000) Nat. Struct. Biol. 7:617. For BoNT/A, a protective belt extending from the translocation domain of the HC wraps around the LC and shields the substrate binding cleft prior to neuronal internalization. See Lacy, D. B., et al. (1998) Nat. Struct. Biol. 5:898. The LC (also referred to as the catalytic domain) separates from the HC under the low pH conditions of the endosome, and acts as a zinc metalloprotease that cleaves SNARE (soluble NSF-ethylmaleimide-sensitive factor attachment protein receptor) proteins. See Turton, K., et al. (2002) Trends. Biochem. Sci. 27:552; and Singh, B. R. (2000) Nat. Struct. Biol. 7:617.

As provided herein, molecular dynamics were used to explore how the motion of residues in and around the BoNT/A LC substrate binding cleft might affect inhibitor binding. In general, the reported analyses support the crystallographically determined structures of BoNT/A LCs that were obtained from the holotoxin PDB 3BTA and PDB 1E1H (two LCs engaged in intermolecular autocatalysis)—α-helices and β-sheets remained stable over the course of the dynamics simulations. See Lacy, D. B., et al. (1998) Nat. Struct. Biol. 5:898; and Segelke, B., et al. (2004) PNAS USA 101:6888. However, the results do suggest that surface loops may reorient to partially shield the substrate binding cleft following LC release from the HC, and that these loop movements may create new binding surfaces for inhibitors, and/or facilitate inhibitor desolvation. See Lacy, D. B., et al. (1998) Nat. Struct. Biol. 5:898; Segelke, B., et al. (2004) PNAS USA 101:6888; and Lacy & Stevens (1999) J. Mol. Biol. 291:1091. Molecular docking studies using previously identified small molecule inhibitors of BoNT/A LC metalloprotease activity have been used to refine our common pharmacophore. See Burnett, J. C., et al. (2003) Biochem. Biophys. Res. Commun. 310:84.

1. Comparisons of BoNT/A LCs Following Dynamics Simulations

As provided in Example 4, two BoNT/A LC structures were examined. One BoNT/A LC was taken from the X-ray crystal structure of the holotoxin, 3BTA BoNT/A LC (Lacy, D. B., et al. (1998) Nat. Struct. Biol. 5:898) and the second was obtained from a recently released X-ray crystal structure of two LCs engaged in intermolecular autocatalysis, 1E1H BoNT/A LC (Segelke, B., et al. (2004) PNAS USA 101: 6888).

With regard to the dimeric 1E1H X-ray crystal structure, BoNT/A LC autocatalysis has been observed in solution, and may occur via an intermolecular route. See Ahmed, S. A., et al. (2001) J. Protein Chem. 20:221; and Ahmed, S. A., et al. (2003) Biochemistry 42:12539, which are herein incorporated by reference. Hence, these atomic coordinates provide evidence to structurally explain a mechanism of intermolecular BoNT/A LC autocatalysis. See Ahmed, S. A., et al. (2001) J. Protein Chem. 20:221; and Ahmed, S. A., et al. (2003) Biochemistry 42:12539, which are herein incorporated by reference.

Following 1 ns of production molecular dynamics, analyses of at least 100 lowest-energy and 10 highest-energy structures from the trajectories of both BoNT/A LCs did not reveal the existence of significantly different conformations of this enzyme as provided in Table 3 as follows:

TABLE 3

Comparisons of BoNT/A LC Structures

| BoNT/A LC structures | RMSD[a] | | |
|---|---|---|---|
| | all | loops 1-3 omitted | only α-helices and β-sheets |
| 3BTA | | | |
| Crystal vs Dynamics avg. | 4.0 Å | 2.7 Å | 1.8 Å |
| Dynamics avg. vs 100 L.E confs.[b] | 0.76 Å[d] | | |
| Dynamics avg. vs 10 H.E. confs.[c] | 0.86 Å[e] | | |
| 1E1H | | | |
| Crystal vs Dynamics avg. | 3.8 Å | 2.4 Å | 1.8 Å |
| Dynamics avg. vs 100 L.E confs. | 0.71 Å[f] | | |
| Dynamics avg. vs 10 H.E. confs. | 0.73 Å[g] | | |
| 3BTA vs 1E1H | | | |
| Crystal vs Crystal | 2.2 Å | 1.1 Å | 0.57 Å |
| Dynamics avg. vs Dynamics avg. | 3.8 Å | 2.4 Å | 1.7 Å |

[a]All superimpositions were performed using backbone atoms
[b]L.E. confs. = lowest energy conformers from the trajectory
[c]H.E. confs. = highest energy conformers from the trajectory
[d]The average rmsd for 100 L.E. confs. from the 3BTA dynamics trajectory compared with the average structure from the same trajectory (rmsd range = 0.64-0.94 Å)
[e]The average rmsd for 10 H.E. confs. from the 3BTA dynamics trajectory compared with the average structure from the same trajectory (rmsd range = 0.70-0.99 Å)
[f]The average rmsd for 100 L.E. confs. from the 1E1H dynamics trajectory compared with the average structure from the same trajectory (rmsd range = 0.61-0.94 Å)
[g]The average rmsd for 10 H.E. confs. from the 1E1H dynamics trajectory compared with the average structure from the same trajectory (rmsd range = 0.63-0.79)

For example, individual superimpositions across all backbone atoms of each of the 100 lowest-energy conformers from the dynamics trajectory of the 3BTA BoNT/A LC with that of the average structure (from the same trajectory) resulted in a mean rmsd of only about 0.76 Å (range=about 0.61 to about 1.0 Å), with a standard deviation of about 0.95

Å. See Table 3. Comparable results were obtained when comparing lowest-energy conformers from the dynamics simulation of the 1E1H BoNT/A LC with the average structure from its trajectory. See Table 3. Additionally, the secondary structures of the 3BTA and 1E1H BoNT/A LC X-ray structures were nearly identical as shown in FIG. 8A, and remained so throughout these analyses. See Table 3.

2. BoNT/A LC Surface Loop Movements

In contrast, the molecular dynamics studies did provide evidence that surface loops bordering the substrate binding clefts of the examined BoNT/A LCs possess the ability to undergo movement that may be important for optimizing inhibitor binding. See Lacy & Stevens (1999) J. Mol. Biol. 291:1091, which is herein incorporated by reference. The surface loops of 3BTA, referred to as: loop 1 (residues 47-80); loop 2 (residues 167-180); and loop 3 (residues 231-259) (FIGS. 8B and 8C), were the main contributors to conformational differences between average structures obtained from the dynamics simulations and original X-ray crystallographic structures (Table 3); for comparison, coordinates of α-helices and β-sheets remained relatively stable over the course of each simulation (Table 3). Interestingly, the observed loop movements in both LC structures, which were solved under different crystallographic conditions, were very similar in nature. Researchers have suggested that conformational changes in surface loops, which are also found in BoNT/B LC X-ray structures, may impact substrate recognition/binding and/or catalysis. See Segelke, B., et al. (2004) PNAS USA 101:6888; Lacy & Stevens (1999) J. Mol. Biol. 291:1091; Hanson & Stevens (2000) Nat. Struct. Biol. 7:687; and Swaminathan & Eswaramoorthy (2000) Nat. Struct. Biol. 7:693. The fact that our analyses indicate the possibility of conformational changes in these loops supports their hypotheses.

Observed loop 1 (residues 47-80) movements during dynamics simulations indicated that this structural feature may play an important role in inhibitor binding. See FIG. 8B and FIG. 8C. Interestingly, during the dynamics simulations of both the 3BTA and the 1E1H BoNT/A LCs, loop 1 possessed the ability to move toward and partially into the substrate binding clefts. Furthermore, it should be noted that the intermolecular lysis observed in the 1E1H structure did not impact loop 1's position in the X-ray crystal structure, and therefore would probably not play a significant role in predetermining the position of this loop.

Taking this information into consideration, the examined BoNT/A LC dynamics trajectories may provide snapshots of possible loop 1 movement. Specifically, the two X-ray crystal structures show loop 1 in a more "open" conformation, allowing for unimpeded access to a solvent exposed cleft; however, dynamics simulations appear to indicate that the natural movement of loop 1 may allow it to reorient toward the LC substrate binding cleft, and it is this relatively more "closed" conformation that may present additional enzyme contacts that facilitate inhibitor or substrate binding. At the same time, loop 1 movement partially shields the cleft from the solvent interface, which might aid the catalytic process. Docking studies of the most potent BoNT/A LC inhibitor to date (a pseudo-peptide possessing a terminal 3-phenyl-2-thiol-propionyl attached via an amide bond to the N-terminus of RATKML ($K_i$=300 nM), and a rationalization of the SAR that accompanies this inhibitor, may be conducted to help clarify which conformation of the enzyme may be the active form. See Schmidt, J. J., et al. (1998) FEBS Lett. 435:61, which is herein incorporated by reference.

Loop 2 (residues 167-180) in the X-ray structure of the 3BTA LC is oriented away from the substrate binding cleft—due to the presence of residues from the translocation domain protective belt. See FIG. 8B. In the absence of the protective belt, this loop adopted a new conformation, i.e., during the dynamics simulations, that brought it into closer association with the substrate binding cleft. Similar orientation of loop 2 toward the substrate binding cleft was also observed for the 1E1H LC. See FIG. 8C. However, loop 2 in the 1E1H X-ray structure was positioned in such a way that it was already oriented toward the substrate binding cleft (as opposed to this loop in the 3BTA BoNT/A LC x-ray structure), thus providing further evidence that this loop is in closer association with the substrate binding cleft following LC release from the HC.

Loop 2 orientation toward the substrate binding cleft may: (1) provide additional ligand contacts and (2) decrease binding cleft solvent accessibility, which would reinforce inhibitor/substrate binding by creating a more favorable environment for desolvation. Indeed, it is possible that the combined movements of both loop 1 and loop 2 help induce the required conformation of the (otherwise flexible) substrate, SNAP 25, which is necessary for optimal binding. From a teleological perspective, perhaps taking advantage of such surface loop movements may have facilitated the evolution of highly toxic and substrate specific BoNT serotypes from a common ancestor.

Loop 3 (residues 231-259) movement observed during dynamics simulations of both examined BoNT/A LCs did not affect accessibility to the enzymes' substrate binding clefts. Both the 3BTA LC loop 3 and the 1E1H LC loop 3 collapsed toward space on the enzyme's surface (FIG. 8B and FIG. 8C) that was originally occupied by either: (1) the holotoxin translocation domain and its protective belt component (in the case of the 3BTA BoNT/A LC) or (2) the loop 3 of the opposing LC in the dimeric structure (in the case of the 1E1H BoNT/A LC).

3. Loop Movements and BoNT/A LC Inhibitor Binding

In a previous report, molecular docking studies were used to define three regions in the BoNT/A LC substrate binding cleft that are hypothesized to be contact sites for identified BoNT/A LC inhibitors. See Burnett, J. C., et al. (2003) Biochem. Biophys. Res. Commun. 310:84, which is herein incorporated by reference. These regions included hydrophobic binding subsite 1 (composed of residues F162, F177, F193, and T219), binding subsite 2 (composed of residues C164, T175, H226, R230, P238, and E270), and a more loosely organized polar contact region (composed of residues E55, Q161, E163, K165, and R176). During these earlier studies, a molecular mechanics refined BoNT/A LC from the 3BTA X-ray crystal structure served as the toxin model. Observed reorientations of BoNT/A LC surface loops bordering the enzyme's substrate binding cleft (during dynamics simulations) are considered with respect to previously specified inhibitor contact subsites in both the 3BTA and the 1E1H BoNT/A LC models.

The composition of binding subsite 1 (also referred to as the $S_1'$ binding site (Segelke, B., et al. (2004) PNAS USA 101:6888; and Schmidt, J. J., et al. (1998) FEBS Lett. 435:61, which are herein incorporated by reference) remained relatively unchanged during the dynamics simulations, as examination of structures from the dynamics trajectories of both the 3BTA LC and the 1E1H LC showed that previously identified residues: F162, F187, F193, and T219 composed this subsite consistently over time. Consequently, binding subsite 1 is a stable pocket where hydrophobic collapse between the enzyme and moieties from our inhibitors, such as a chloro, methyl, methoxy, or a dihydro imidazolyl, is likely to occur. For example, when one of our previously identified inhibitors, Q2-15 (about 60% inhibition at 20 μM conc.), is docked into either a structure from the 1E1H BoNT/A LC dynamics trajectory, or the mechanics refined X-ray structure of 1E1H, one of the chloro substituents engages in favorable contacts with the hydrophobic side-chains of residues in subsite 1. See FIG. 9A and FIG. 9B. At the same time, the accompanying quinoline nitrogen is positioned in close proximity to the enzyme's catalytic engine, where it may either engage in a direct interaction with the zinc ion, or displace the engine's catalytic water. In a similar manner, FIG. 10A and FIG. 10B show how the methoxy and methyl substituents of michellamine B (about 62% inhibition at 20 μM conc.) naphthalene ring A engage in favorable hydrophobic interactions with residues of binding subsite 1 in both a structure from the 3BTA dynamics simulation and the mechanics refined X-ray structure of 3BTA, respectively. Additionally, as observed for the quinoline nitrogen of Q2-15, the hydroxyl moiety of naphthalene ring A may interact directly with the enzyme's catalytic zinc, or displace the water that is used by the enzyme's catalytic engine.

The binding mode of Q2-15 in the dynamics structure of 1E1H also shows that loop 1 orientation towards the enzyme's substrate binding cleft creates a new hydrophobic pocket near subsite 1 (composed of residues K65 (hydrophobic side-chain), V67, and P68), which provides a complimentary binding surface for three methylene carbons that form half of the flexible linker connecting the inhibitor's two 7-chloroquinoline components. See FIG. 9A. These additional hydrophobic contacts are not observed when Q2-15 is docked in the more "open" mechanics refined structure. See FIG. 9B. In like manner, michellamine B binding in the 3BTA dynamics structure as shown in FIG. 10A shows the methyl substituent of naphthalene ring A engaging in a hydrophobic contact with Val 67 (this contact is not observed when michellamine B is docked in the 3BTA mechanics refined structure as shown in FIG. 10B).

The solvent accessibility of binding subsite 2 is reduced during the dynamics simulation of the 3BTA structure—due to loop 2 movement (as indicated above, loop 2 was already oriented toward the substrate binding cleft in the 1E1H X-ray crystal structure). However, these changes had little affect on the amino acids composing this subsite: C164, H226, R230, E270, and P238 remained key residues surrounding this pocket. FIG. 9A and FIG. 9B show how Q2-15 binding within this subsite is very similar in both the 1E1H dynamics structure and the 1E1H mechanics refined X-ray structure, respectively. Specifically, the other Q2-15 chloroquinoline moiety docks in this subsite in such a way that the quinoline ring sits in close proximity to the side-chain of R230 (with the quinoline nitrogen pointed toward that solvent interface), while the 7-chloro substituent of this moiety points into the binding subsite and engages in favorable hydrophobic contacts with the side-chain imidazole of H226 and the methylenes of E270.

Loop 2 reorientation is more dramatic when comparing michellamine B docked in the 3BTA dynamics structure (FIG. 10A) and the mechanics refined structure (FIG. 10B). FIG. 4A shows how loop 2 reorientation increases the depth of this subsite—compared to the crystal structure (FIG. 10B)—with the entire loop rising as it moved toward the enzyme's binding cleft. As a result, a new boundary for this end of the substrate binding pocket is created, and solvent accessibility is reduced. With regard to michellamine B binding in subsite 2, the methoxy substituent of naphthalene ring B packs into space located behind H226 (in a manner similar to one of the chloro substituents of Q2-15) in both the 3BTA dynamics structure and the mechanics refined X-ray crystal structure. In contrast, the methyl substituent on naphthalene ring B in the dynamics structure sits behind loop 2 and engages in hydrophobic contacts with the side-chain methylenes of residue E170 (FIG. 10A), while this same substituent in the molecular mechanics refined structure of 3BTA is more solvent exposed (FIG. 10B).

Residues in the previously identified polar contact region (composed of residues E55, Q161, E163, L165, and R176 for inhibitors also remained consistent over the course of the dynamics trajectory. However, loop 1 reorientation partially covers this contact region, leaving it less solvent accessible, and also brings new contact residues into association with this binding region.

Models of Q2-15 docked in both the BoNT/A LC dynamics structure (FIG. 9A) and the mechanics refined X-ray structure (FIG. 9B) indicate that the inhibitors ionizable secondary nitrogen engages in a hydrogen bond with the side-chain carboxylate of E163. Furthermore, due to loop 1 reorientation in the dynamics structure, the inhibitor's secondary nitrogen also engages in an ion-dipole interaction with the backbone carbonyl of K65. See FIG. 9A. For comparison, the ionizable nitrogen of the michellamine B tetrahydro-isoquinoline moiety attached to naphthalene ring B engages in a hydrogen bond with the side-chain carboxylate of residue E55, and is also in close proximity to the side chain carboxylate of E163, in both the dynamics (FIG. 10A) and molecular mechanics refined (FIG. 10B) models of 3BTA. Furthermore, in the 3BTA dynamics structure (FIG. 10A), loop 1 reorientation resulted in additional residue contacts with the 1,3-dimethyl-1,2,3,4-tetrahydro-isoquinoline-6,8-diol moiety attached to naphthalene ring B. Specifically, the side-chain carboxylate of E63 is located near the ionizable nitrogen of the 1,3-dimethyl-1,2,3,4-tetrahydro-isoquinoline-6,8-diol moiety, and engages in a hydrogen bond with the 8-hydroxyl substituent, while the moieties 3-methyl substituent engages in a hydrophobic interaction with the P61 pyrrolidine.

In general, Q2-15 and michellamine B, although structurally very different, engage in similar contacts in the BoNT/A LC substrate binding cleft—regardless of the enzyme model that is used. These two compounds also map well to the pharmacophore of the present invention which would seem to explain their comparable inhibitory potency. Furthermore, analyses of inhibitors docked in the dynamics structures, versus mechanics refined X-ray crystal structures of both 1E1H and 3BTA, indicate that the models obtained from the dynamics simulations provide additional inhibitor contacts that may be important for inhibitor binding. In particular, additional hydrophobic contacts near subsite 1, additional contacts at the polar contact region, and a reduction in the solvent accessibility at subsite 2 (following loop 2 reorientation toward the substrate binding cleft) all seem to suggest that possible loop reorientations toward the BoNT/A LC substrate binding cleft may be important for understanding inhibitor/substrate binding, and consequently, for the future development of small molecule inhibitors.

4. Potential Silver Ion Binding Sites

Silver ion inhibits BoNT/A LC metalloprotease activity (about 100% inhibition at equal to or greater than about 5 μM) without displacing the catalytic zinc ion or causing enzyme denaturation as disclosed herein. See also Burnett, J. C., et al. (2003) Biochem. Biophys. Res. Commun. 310:84, which is herein incorporated by reference. Observed loop 1 movement toward the substrate binding cleft may aid in partially explaining these results. In particular, FIG. 11 shows how loop 1 reorientation in the 3BTA dynamics structure creates a pocket that could potentially trap a silver ion. In FIG. 11, a silver ion is shown engaging in an ionic interaction with the side-chain carboxylate of D158, and ion dipole interactions with the side-chain amide carbonyl of Q161, and the backbone carbonyl oxygens of V69 and I160. In addition to the above contacts, the silver ion might also interact with other residues in the polar contact region, including E163. It should also be noted that binding subsite 2 may provide a potential silver ion contact region, with the ion coordinated to the C164 side-chain thiol, and engaging in electrostatic interactions with surrounding residues H226 and E270. Interestingly, there are no other regions in or near the substrate binding cleft that would provide similar clusters of residues for silver ion "trapping".

5. Refinement of the BoNT/A LC Inhibitor Pharmacophore

FIG. 12 shows the components of the pharmacophore for BoNT/A LC inhibition as provided herein. Components A and B in FIG. 12 represent two planar moieties, one of which contains a heteroatom that may engage in an interaction with the enzyme's catalytic zinc, or potentially replace the water used by the zinc during substrate lysis. Examples of components A and B include the two-quinoline rings of Q2-15 (FIGS. 7, 9A, and 9B) and the two naphthalene rings of michellamine B (FIGS. 7, 10A, and 10B). In FIG. 12, pharmacophore components C and D are two hydrophobic substituents, which are predicted to interact with subsites 1 and 2 in the substrate binding cleft, respectively. Examples of components C and D include the two chloro substituents of Q2-15 and the methoxy substituents (attached to the naphthalene rings) of michellamine B. Finally, the polar, ionizable pharmacophore component E (FIG. 12) is hypothesized to either engage in electrostatic or water mediated interactions with residues in the polar contact region. Examples of component E include the secondary nitrogen of Q2-15 and the secondary nitrogen of one of the tetrahydroisoquinolines of michellamine B.

Comparisons between inhibitors docked in molecular dynamics models (FIGS. 9A and 10A) and inhibitors docked in molecular mechanics refined models (FIGS. 9B and 10B) indicate that inhibitor residue contacts in binding subsites 1 and 2, and the polar contact region, remain relatively consistent during the movement of BoNT/A LC residues. Moreover, analyses indicate that loop reorientations may bring additional residues into play, which may serve to facilitate inhibitor binding. Based on these observations, the BoNT/A LC inhibitor pharmacophore is refined via the addition of residues that are predicted to interact with specified pharmacophore components. See FIG. 12. These residues will be important for the purpose of molecular docking of compounds identified using the pharmacophore parameters. Hence, the fit of these molecules to the binding pocket of the BoNT/A LC may be predicted (using molecular modeling) before testing in vitro using methods known in the art.

CATALYST® software allows mapping of all functions generated in a pharmacophore to the more potent analogues and fewer or none in the less potent analogues of the training set through conformational energy and best-fit scoring calculations. The technique involves a 3D screening of all the conformations of the molecule by matching the pharmacophore features. See Kurogi, Y and Gunner, OF (2001) Current Medicinal Chemistry 8:1035-1055, which is herein incorporated by reference.

Although CATALYST® 4.7 software (Accelrys Inc., San Diego, Calif.) may be used for 3D QSAR analysis and pharmacophore generation, other methods known in the art such as those described in PHARMACOPHORE PERCEPTION, DEVELOPMENT, AND USE IN DRUG DESIGN (2000) Ed. Osman F. Gunner, International University Line, La Jolla, Calif., which is herein incorporated by reference, may be used according to the present invention.

As disclosed in Example 5, molecular modeling software, CATALYST® 4.7 software (Accelrys Inc., San Diego, Calif.) may be used to construct three-dimensional QSAR pharmacophore models for the repellent activities exhibited by some repellent compounds known in the art. A training set of comprising the small molecule inhibitors disclosed herein may be used to construct a 3D QSAR pharmacophore model. Although more or less compounds in the training set may be used, in preferred embodiments, about 10 to about 20 chemically diverse molecules with biological activity covering 4 to 5 orders of magnitude for the training set are preferred.

The structures of the training set may be either imported into or edited within CATALYST® by assembling the structural fragments and energy minimized to the closest local minimum using the CHARMM-like force field. Molecular flexibility may be taken into account by considering each compound as an ensemble of conformers representing different accessible areas in a three dimensional space. The "best searching procedure" may be applied to select representative conformers within about 20 kcal/mol above the calculated global minimum. See Grigorov, M, et al. (1995) J. Chem. Inf. Comput. Sci. 35:285-304, which is herein incorporated by reference.

Hypothesis generation may be carried out with the training set by methods known in the art. See Greenridge, P A and J. Weiser (2001) Mini Reviews in Medicinal Chemistry 1:79-87; Grigorov, M, et al (1995) J. Chem. Inf. Comput. Sci. 35:285-304; which are herein incorporated by reference. The coordinates of a pharmacophore model are dependent upon the particular coordinate system used, and those skilled in the art will recognize that, although rotation and translation of these coordinates may change the specific values of these coordinates, they will in fact define the pharmacophore model of the present invention. The pharmacophore model of the present invention is intended to encompass any model, after optimal superposition of the models, comprising the identified features and having a root mean square of equivalent features of less than about 3.0 Å. More preferably, the pharmacophore model of the present invention encompasses any model comprising the features identified herein and having a root mean square of equivalent features of less than about 1.5 Å, even more preferably, less than about 1.0 Å, and most preferably less than about 0.5 Å.

As those of skill in the art will readily recognize, chemically different substructures can present certain identical three-dimensional space-filling features, and accordingly, the models of the present invention comprise features that may or may not correspond to actual functional groups in any given compound. Additionally, since compounds having different structural formulas may have the same or similar pharmacophore hypotheses, the compounds of the present invention are not limited to compounds having similar chemical structures.

As provided in Example 6, the pharmacophore model may be cross-validated by using a test set of compounds known in the art. The test set compounds may be screened for the ability to inhibit Botulinum neurotoxin A metalloprotease activity by the assays provided herein or other methods known in the art and then compared with the activity of those compounds in the original training set. The validity of the pharmacophore model to other compounds found to inhibit Botulinum neurotoxin A metalloprotease activity may be examined. The pharmacophore features may be mapped onto the compounds and should be found to map significantly well with known compounds to varying degrees.

There are 3 parameters such as the "best-score fit", estimate of activity, and conformational energy costs are involved in the present case to assess the quality of the pharmacophore mapping. The mapping of a pharmacophore on the three-dimensional structure of a compound is carried out by means of a few calculations. The compound to be mapped to a pharmacophore is converted to a three-dimensional configuration and all its conformations with energies are stored in a computer which then performs the analytical calculations which compares the three-dimensional conformers of the compound being mapped and the pharmacophore. Perfect mapping means that the features of the pharmacophore matches exactly with at least one of the conformers of the compound. "Best-fit scores" indicate the degree of matching, conformational energy indicates how much of energy would be spent by the molecule to match the pharmacophore, and estimate of activity is the prediction of activity should the compound be a member of the training set from the pharmacophore was originally developed.

The pharmacophore model of the present invention may be used to search three-dimensional multiconformer databases and other chemical databases, including an in-house Chemical Information System (Chemical Information System, Division of Experimental Therapeutics, Walter Reed Army Institute of Research, Silver Spring, Md.), National Cancer Institute, IBS and Maybridge databases, to screen for compounds that inhibit Botulinum neurotoxin A metalloprotease activity. A chemical database may be transformed into a multiconformer database in CATALYST® using the catDB® utility program as implemented in the software. The catDB® format allows a molecule to be represented by a limited set of conformations thereby permitting conformational flexibility to be included during the search of the database.

The pharmacophore models of the present invention can be used to evaluate repellent activity and potency of a candidate compound. The candidate compounds being evaluated may be designed de novo using the models of the invention, or alternatively, be a compound, e.g., chosen from a library of compounds. Using the pharmacophore model of the invention and the methods of identification disclosed herein, one may predict the activity of a candidate compound based upon its fit with the pharmacophore model of the invention. Further, one may even predict the relative degree of activity via the methods of the invention by calculation of the $K_1$ (apparent) value for a compound.

After identifying a candidate compound to be evaluated for the ability to inhibit Botulinum neurotoxin A metalloprotease, the three-dimensional structure of the compound may be determined. This may already have been done if, e.g., the compound was obtained from a structural database wherein three-dimensional x, y and z coordinates were used to define the compound. Alternatively, the three-dimensional structures of small molecules can be readily determined by methods known to those of skill in the art, including but not limited to, X-ray crystallography, nuclear magnetic resonance spectrometry, and the like. The structures obtained from structural databases are usually the structures of compounds alone, uncomplexed with other molecules. If the three-dimensional structure is not known, one may use computer programs, such as CATALYST®, to predict the three-dimensional structure of the compound. Three-dimensional conformers may be generated from a starting structure using methods well known in the art such as Best or Fast Conformational Analyses (Molecular Simulations, Inc., San Diego, Calif.) with an energy set to a range of 0 to 50 Kcal/mol, preferably 0 to 35 Kcal/mole, and most preferably 0 to 10 Kcal/mole, and the maximum number of conformations set to 100, preferably 175, and most preferably 255. The pharmacophore model may be then compared to a given compound using tools to compare the structural features of each, such as COMPARE™ within the VIEW HYPOTHESIS™ workbench (Molecular Simulations, Inc., San Diego, Calif.).

The degree of fit of a particular compound structure to the pharmacophore model may be calculated by determining, using computer methods, if the compound possesses the chemical features of the model and if the features can adopt the necessary three-dimensional arrangement to fit the model. The modeling program will indicate those features in the model having a fit with the particular compound.

In preferred embodiments, the present invention encompasses compounds that exhibit the ability to inhibit Botulinum neurotoxin A metalloprotease activity and map well to the pharmacophore model disclosed herein. For example, methods for suitably superimposing compounds on a three-dimensional representation of the pharmacophore model of the present invention using computational methods is well known to those of skill in the art. A superposition of structures and the pharmacophore model is defined as a minimization of the root mean square distances between the centroids of the corresponding features of the molecule and the pharmacophore. A Van der Waals surface is then calculated around the superimposed structures using a computer program such as CERIUS™ (Molecular Simulations, Inc., San Diego, Calif.).

The compounds of the present invention may be made according to methods known in the art.

In accordance with a convention used in the art, and "—" as, for example, in "—R" are used in structural formulas herein to depict the bond that is the point of attachment of the moiety or substituent to the core or backbone structure.

Where chiral carbons are included in chemical structures, unless a particular orientation is depicted, both sterioisomeric forms are intended to be encompassed.

A "heteroatom" is any atom that is not carbon or hydrogen and includes nitrogen, oxygen, sulfur, phosphorus, boron, and the like. In preferred embodiments, the heteroatoms in the compounds of the present invention are N, O, or S.

An "ionizable substituent" is one which forms a charge depending on the surrounding pH of the solvent and includes carboxylates, primary, secondary, and tertiary amines, the quanadino substituents, aromatic nitrogents with four bonds, a hydroxyl moiety attached to an aromatic ring, and the like. In preferred embodiments, the ionizable substituents in the compounds of the present invention are primary, secondary, tertiary amines, and quaternary amines, quanadion substituents, and aromatic nitrogens with four bonds.

A "hydrophobic moiety" is intended to mean a lipophilic moiety that incurs a thermodynamic penalty for being exposed to solvent and includes alkyl groups, bromo, chloro, and iodo substituents, and the like. In preferred embodiments, the hydrophobic moieties in the compounds of the present invention are chloro, bromo, and iodo substituents, and methoxy, methyl, and unsaturated heterocycles.

An "alkyl" is intended to mean a straight or branched chain monovalent radical of saturated and/or unsaturated carbon atoms and hydrogen atoms, such as methyl (Me), ethyl (Et), propyl (Pr), isopropyl (i-Pr), butyl (n-Bu), isobutyl (i-Bu), t-butyl (t-Bu), (sec-Bu), ethenyl, pentenyl, butenyl, propenyl, ethynyl, butynyl, propynyl, pentynyl, hexynyl, and the like, which may be unsubstituted (i.e., contain only carbon and hydrogen) or substituted by one or more suitable sustituents as defined below (e.g., one or more halogen, such as F, Cl, Br, or I, with F and Cl being preferred). A "lower alkyl group" is intended to mean an alkyl group having from 1 to 8 carbon atoms in its chain.

A "cycloalkyl" is intended to mean a non-aromatic monovalent monocyclic, bicyclic, or tricyclic radical comprising 3-14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents. Illustrative examples of cycloalkyl groups include the following moieties:

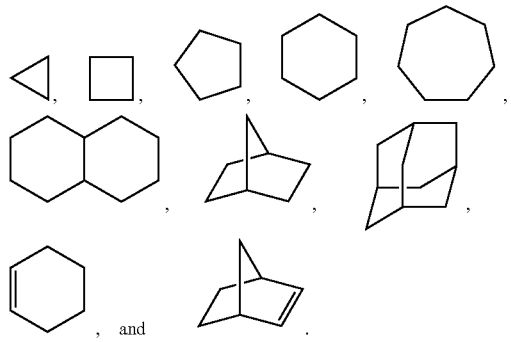

A "heterocycloalkyl" is intended to mean a non-aromatic monovalent monocyclic, bicyclic, or tricyclic radical, which is saturated or unsaturated, comprising 3-18 ring members, which includes 1-5 heteroatoms selected from nitrogen, oxygen, and sulfur, where the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include the following moieties:

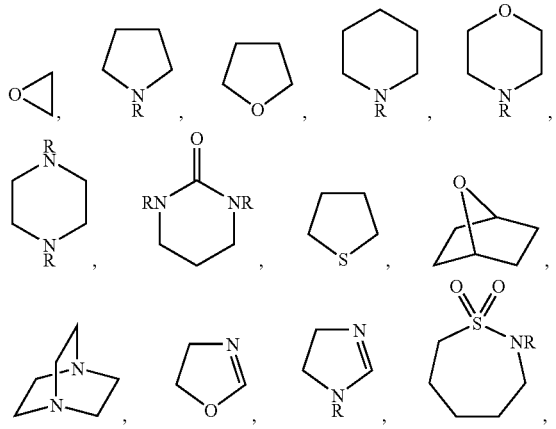

-continued

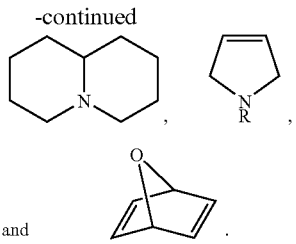

An "aryl" is intended to mean an aromatic monovalent monocyclic, bicyclic, or tricyclic radical comprising 6, 10, 14, or 18 carbon ring members, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Illustrative examples of aryl groups include the following moieties:

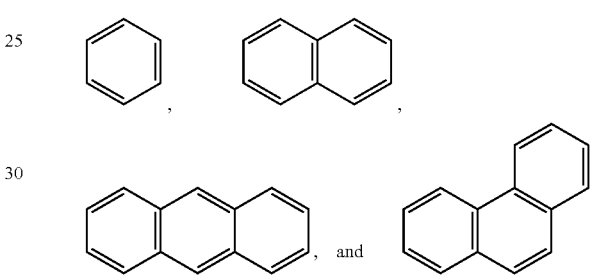

A "biaryl" is intended to mean an aromatic system composed of two rings and includes naphthalene, quinoline, isoquinoline, and the like. In preferred embodiments, biaryls in the compounds of the present invention include naphthalene, quinoline, isoquinoline, benzofuran, indole, quinazoline, quinoxaline, naphthyridine, phthalazine, or purine.

A "triaryl" is intended to mean an aromatic system composed of three rings and includes acridine, carbazole, phenazine, and the like. In preferred embodiments, triaryls in the compounds of the present invention include acridine, phenazine, phenanthroline, phenanthridine or carbazole.

A "heteroaryl" is intended to mean an aromatic monovalent monocyclic, bicyclic, or tricyclic radical comprising 4-18 ring members, including 1-5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include the following moieties:

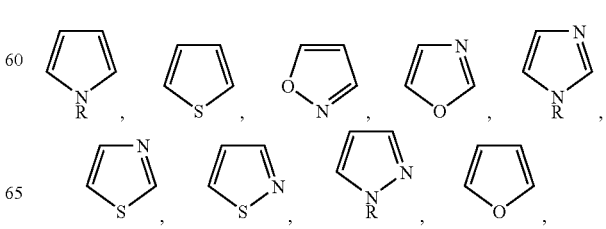

A "heterocycle" is intended to mean a heteroaryl or heterocycloalkyl group (each of which, as defined above, are optionally substituted).

The terms "aryl" (Ar) and "heteroaryl" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like.

An "acyl" is intended to mean a —C(O)—$R^a$ radical, where $R^a$ is a suitable substituent as defined below.

A "thioacyl" is intended to mean a —C(S)—$R^a$ radical, where $R^a$ is a suitable substituent as defined below.

A "sulfonyl" is intended to mean a —$SO_2R^a$ radical, where $R^a$ is a suitable substituent as defined below.

A "hydroxyl" is intended to mean the radical —OH.

An "amino" is intended to mean the radical —$NH_2$.

An "alkylamino" is intended to mean the radical —$NHR^a$, where $R^a$ is an alkyl group.

A "dialkylamino" is intended to mean the radical —$NR^aR^b$, where $R^a$ and $R^b$ are each independently an alkyl group.

An "alkoxyl" is intended to mean the radical —$OR^a$, where $R^a$ is an alkyl group. Exemplary alkoxyl groups include methoxyl, ethoxyl, propoxyl, and the like.

An "alkoxycarbonyl" is intended to mean the radical —C(O)$OR^a$, where $R^a$ is an alkyl group.

An "alkylsulfonyl" is intended to mean the radical —$SO_2R^a$, where $R^a$ is an alkyl group.

An "alkylaminocarbonyl" is intended to mean the radical —C(O)$NHR^a$, where $R^a$ is an alkyl group.

A "dialkylaminocarbonyl" is intended to mean the radical —C(O)$NR^aR^b$, where $R^a$ and $R^b$ are each independently an alkyl group.

A "mercapto" is intended to mean the radical —SH.

An "alkylthio" is intended to mean the radical —$SR^a$, where $R^a$ is an alkyl group.

A "carboxyl" is intended to mean the radical —C(O)OH.

A "carbamoyl group" is intended to mean the radical —C(O)$NH_2$.

An "aryloxyl" is intended to mean the radical —$OR^c$, where $R^c$ is an aryl group.

A "heteroaryloxyl" is intended to mean the radical —$OR^d$, where $R^d$ is a heteroaryl group.

An "arylthio" is intended to mean the radical —$SR^c$, where $R^c$ is an aryl group.

A "heteroarylthio" is intended to mean the radical —$SR^d$, where $R^d$ is a heteroaryl group.

A "leaving group" (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

A "protecting group" is intended to refer to groups that protect one or more inherent functional group from premature reaction. Suitable protecting groups may be routinely selected by those skilled in the art in light of the functionality and particular chemistry used to construct the compound. Examples of suitable protecting groups are described, for example, in Greene and Wuts, Protective Groups in Organic Synthesis, 3$^{rd}$ edition, John Wiley and Sons, New York, N.Y. (1999).

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxyl groups, carboxyl groups, amino groups, alkylamino groups, dialkylamino groups, carbamoyl groups, arylthio groups, heteroarylthio groups, and the like.

In general, the various moieties or functional groups for variables in the formulae may be "optionally substituted" by one or more suitable "substituents". The term "substituent" or "suitable substituent" is intended to mean any suitable substituent that may be recognized or selected, such as through routine testing, by those skilled in the art. Illustrative examples of useful substituents are those found in the exemplary compounds that follow, as well as halogen (chloro, iodo, bromo, or fluoro); $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O. All of these substituents may optionally be further substituted with a substituent selected from groups such as hydroxyl groups, halogens, oxo groups, alkyl groups, acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, alkylamino groups, dialkylamino groups, carbamoyl groups, aryloxyl groups, heteroaryloxyl groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

It is understood that while a compound of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Some of the compounds of the present invention may exist as single stereoisomers (i.e., essentially free of other stereoisomers), racemates, or mixtures of enantiomers, diastereomers, or both. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, if the compounds of the present invention are made synthetically, they are used in a form that is at least 90% optically pure, that is, a form that comprises at least 90% of a single isomer (80% enantiomeric excess (e.e.) or diastereomeric excess (d.e.), more preferably at least 95% (90% e.e. or d.e.), even more preferably at least 97.5% (95% e.e. or d.e.), and most preferably at least 99% (98% e.e. or d.e.).

Additionally, the structural formulas herein are intended to cover, where applicable, solvated as well as unsolvated forms of the compounds. A "solvate" is intended to mean a pharmaceutically acceptable solvate form of a specified compound that retains the biological effectiveness of such compound. Examples of solvates include compounds of the invention in combination with water, isopropanol, ethanol, methanol, dimethyl sulfoxide, ethyl acetate, acetic acid, ethanolamine, or acetone. Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulas include compounds having the indicated structure, including the hydrated as well as the non-hydrated forms.

As indicated above, the compounds of the invention also include active tautomeric and stereoisomeric forms of the compounds of the present invention, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

Additionally, the compounds of the invention include pharmaceutically acceptable salts, multimeric forms, prodrugs, active metabolites, precursors and salts of such metabolites of the compounds of the present invention.

The term "pharmaceutically acceptable salts" refers to salt forms that are pharmacologically acceptable and substantially non-toxic to the subject being treated with the compound of the invention. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

The term "multimer" refers to multivalent or multimeric forms of active forms of the compounds of the invention. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to receptor binding. Provision of such multivalent forms of active receptor-binding compounds with optimal spacing between the receptor-binding moieties may enhance receptor binding. See e.g. Lee, et al., (1984) Biochem. 23:4255. The artisan may control the multivalency and spacing by selection of a suitable carrier moiety or linker units. Useful moieties include molecular supports comprising a multiplicity of functional groups that can be reacted with functional groups associated with the active compounds of the invention. A variety of carrier moieties may be used to build highly active multimers, including proteins such as BSA (bovine serum albumin), peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound. "A pharmaceutically active metabolite" is intended to mean a pharmacologically active product produced through metabolism in the body of a specified compound or salt thereof. Prodrugs and active metabolites of a compound may be identified using routine techniques known in the art. See e.g., Bertolini, G, et al., (1997) J. Med. Chem. 40:2011-2016; Shan, D, et al., *J. Pharm. Sci.,* 86(7):765-767; Bagshawe K (1995) Drug Dev. Res. 34:220-230; Bodor, N (1984) Advances in Drug Res. 13:224-331; Bundgaard, H *Design of Prodrugs* (Elsevier Press, 1985); and Larsen, I. K., *Design and Application of Prodrugs*, Drug Design and Development (Krogsgaard-Larsen et al., eds., Harwood Academic Publishers, 1991).

If the compound of the present invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrvic acid, oxalic acid, glycolic acid, salicylic acid, a pyranosidyl acid, such as glucuronic acid or galacturonic acid, an α-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the present invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from basic amino acids, such as lysine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of compounds that are solids, it is understood by those skilled in the art that the compound of the present invention and salts may exist in different crystal or polymorphic forms, all of which are intended to be within the scope of the present invention and specified structural formulas.

The specification for the dosage unit forms of the invention are dictated by and directly dependent on the unique characteristics of the active compound and the limitations inherent in the art of compounding such an active compound for the treatment of individuals. In general, formulations containing greater concentrations of active ingredient provide more effective and long-lasting protection.

A compound of the present invention may be administered in an effective amount to a mammal such as a human. An "effective amount" is intended to mean that amount of a given repellent compound that is sufficient to inhibit Botulinum neurotoxin A metalloprotease activity as compared to a control. The amount of a given compound of the present invention that will correspond to such an amount will vary depending upon factors such as the given compound, the pharmaceutical or cosmetic formulation and route of administration, and the like, but can nevertheless be routinely determined by one skilled in the art. An "effective amount" of a compound of the present invention may be readily determined by one of ordinary skill by routine methods known in the art. As used herein, an "effective amount" refers to an amount that provides an observable desired change as compared with a control. For example, if the desired change is a decrease the amount of a given protein and administration of 0.9 µM of a compound does not produce an observable decrease as compared with a control, but the administration of 1 µM does produce an observable decrease, then the effective amount is about 1 µM or more.

A therapeutically effective amount may be readily determined by standard methods known in the art. As defined herein, a therapeutically effective amount of a compound of the invention ranges from about 0.1 to about 25.0 mg/kg body weight, preferably about 1.0 to about 20.0 mg/kg body weight, and more preferably about 10.0 to about 20.0 mg/kg body weight. Preferred topical concentrations include about 0.1% to about 20.0% in a formulated salve.

The skilled artisan will appreciate that certain factors may influence the dosage required to effectively treat a subject, including but not limited to the severity of toxicity and exposure, previous treatments, the general health and/or age of the subject, and other diseases present. Moreover, treatment of a subject with a therapeutically effective amount of the compound can include a single treatment or, preferably, can include a series of treatments.

Methods for treating toxicity and exposure to Botulinum neurotoxin according to the present invention may consist of a single administration of a least one compound of the present invention, or alternatively comprise a series of administrations. For example, a subject may be treated with a compound of the present invention at least once. However, the subject may treated with the compound from about one time per week to about once daily or multiple times daily for a given treatment period. The length of the treatment period will depend on a variety of factors that may be readily determined by one skilled in the art.

In a preferred example, a subject is treated with a compound of the invention in the range of between about 0.1 to about 25.0 mg/kg body weight, at least one time per week for between about 5 to about 8 weeks, and preferably between about 1 to about 2 weeks. It will also be appreciated that the effective dosage of the compound used for treatment may increase or decrease over the course of a particular treatment. Changes in dosage may result and become apparent by standard diagnostic assays known in the art. In some conditions chronic administration may be required.

The pharmaceutical and cosmetic formulations of the invention comprise at least one compound of the present invention and may be prepared in a unit-dosage form appropriate for the desired mode of administration. The pharmaceutical formulations of the present invention may be administered by any suitable route including oral, rectal, nasal, topical (including buccal and sublingual), vaginal and parenteral (including subcutaneous, intramuscular, intravenous and intradermal). In preferred embodiments, the compounds of the present invention are topically administered to a subject or placed on or integrated into an object from which a given pest is to be repelled.

The formulations of the present invention comprise an effective amount of at least one compound of the present invention, and an inert, pharmaceutically or cosmetically acceptable carrier or diluent. As used herein the language "pharmaceutically or cosmetically acceptable carrier" is intended to include any and all solvents, dispersion media, coatings, antibacterial and antifungal agents, isotonic and absorption delaying agents, and the like, compatible with pharmaceutical or cosmetic administration. The pharmaceutical or cosmetic carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like. The use of such media and agents for pharmaceutically or cosmetically active substances is well known in the art.

Except insofar as any conventional media or agent is incompatible with the active compound, use thereof in the formulation is contemplated. Supplementary active compounds can also be incorporated into the formulations. Supplementary active compounds include antibiotics, antiprotozoal agents, antifungal agents, and antiproliferative agents known in the art, analgesics and other compounds commonly used to treat diseases and disorders associated with given pests to be repelled.

Antibiotics include penicillin, cloxacillin, dicloxacillin, methicillin, nafcillin, oxacillin, ampicillin, amoxicillin, bacampicillin, azlocillin, carbenicillin, mezlocillin, piperacillin, ticarcillin, azithromycin, clarithromycin, clindamycin, erythromycin, lincomycin, demeclocycline, doxycycline, minocycline, oxytetracycline, tetracycline, quinolone, cinoxacin, nalidixic acid, fluoroquinolone, ciprofloxacin, enoxacin, grepafloxacin, levofloxacin, lomefloxacin, norfloxacin, ofloxacin, sparfloxacin, trovafloxacin, bacitracin, colistin, polymyxin B, sulfonamide, trimethoprim-sulfamethoxazole, co-amoxyclav, cephalothin, cefuroxime, ceftriaxone, vancomycin, gentamicin, amikacin, metronidazole, chloramphenicol, nitrofurantoin, co-trimoxazole, rifampicin, isoniazid, pyrazinamide, kirromycin, thiostrepton, micrococcin, fusidic acid, thiolactomycin, fosmidomycin, and the like.

Antiprotozoal agents include chloroquine, doxycycline, mefloquine, metronidazole, eplornithine, furazolodone, hydroxychloroquine, iodoquinol, pentamidine, mebendazole, piperazine, halofantrine, primaquine, pyrimethamine sulfadoxine, doxycycline, clindamycin, quinine sulfate, quinidine gluconate, quinine dihydrochloride, hydroxychloroquine sulfate, proguanil, quinine, clindamycin, atovaquone, azithromycin, suramin, melarsoprol, eflornithine, nifurtimox, amphotericin B, sodium stibogluconate, pentamidine isethionate, trimethoprim-sulfamethoxazole, pyrimethamine, sulfadiazine, and the like.

Antifungal agents include amphotericin B, fluconazole, itraconazole, ketoconazole, potassium iodide, flucytosine, and the like.

Antiproliferative agents such as altretamine, amifostine, anastrozole, arsenic trioxide, bexarotene, bleomycin, busulfan, capecitabine, carboplatin, carmustine, celecoxib, chlorambucil, cisplatin, cisplatin-epinephrine gel, cladribine, cytarabine liposomal, daunorubicin liposomal, daunorubicin daunomycin, dexrazoxane, docetaxel, doxorubicin, doxorubicin liposomal, epirubicin, estramustine, etoposide phosphate, etoposide VP-16, exemestane, fludarabine, fluorouracil 5-FU, fulvestrant, gemcitabine, gemtuzumab-ozogamicin, goserelin acetate, hydroxyurea, idarubicin, ifosfamide, imatinib mesylate, irinotecan, letrozole, leucovorin, levamisole, liposomal daunorubicin, melphalan L-PAM, mesna, methotrexate, methoxsalen, mitomycin C, mitoxantrone, paclitaxel, pamidronate, pegademase, pentostain, porfimer sodium, streptozocin, talc, tamoxifen, temozolamide, teniposide VM-26, topotecan, toremifene, tretinoin, ATRA, valrubicin, vinorelbine, zoledronate, steroids, and the like.

Supplementary compounds also include antidotes known in the art such as antitoxins that neutralize biological toxins such as the available trivalent antitoxin for botulinum serotypes A, B, and E (available from the CDC) (Amon, S. S., et al. (2001) JAMA 284:1059-1070, which is herein incorporated by reference); the investigational heptavalent botulinum (ABCDEFG) antitoxin held by the U.S. Army (Hibbs, R. G., et al. (1996) Clin. Infect. Dis. 23:337-340); the anthrax vaccine currently available to military personnel (Greenfield & Bronze (2003) Drug Discovery Today 8:881-888); polyclonal and monoclonal antibodies against anthrax toxin, including those antibodies generated in both animals or through techniques that produce partially human or totally human sequences (Greenfield R A & Bronze M S (2003) Drug Discovery Today 8:881-888); polyclonal antibodies and monoclonal antibodies (both single and in synergistic mixtures) that inhibit botulinum neurotoxins (including those antibodies produced in animals or using technologies that generate partial or totally human sequences (Marks, J. D. (2004) Movement Disorders 19:S101-S108; Pless, D. D. et al. (2001) Infection and immunity 69:570-574), and the like.

The formulations of the invention may be manufactured in manners generally known for preparing pharmaceutical and cosmetic compositions, e.g., using conventional techniques such as mixing, dissolving, granulating, dragee-making, levigating, emulsifying, encapsulating, entrapping or lyophilizing. The formulations may be formulated in a conventional manner using one or more physiologically acceptable carriers, which may be selected from excipients and auxiliaries that facilitate processing of the active compounds into preparations which can be used pharmaceutically or cosmetically.

For topical formulations of the present invention, pharmaceutically acceptable excipients or cosmetically acceptable carriers and additives include solvents, emollients, humectants, preservatives, emulsifiers, pH agents, and the like. Suitable solvents include ethanol, acetone, glycols, polyurethanes, and others known in the art. Suitable emollients include petrolatum, mineral oil, propylene glycol dicaprylate, lower fatty acid esters, lower alkyl ethers of propylene glycol, cetyl alcohol, cetostearyl alcohol, stearyl alcohol, stearic acid, wax, face paints, and others known in the art. Suitable humectants include glycerin, sorbitol, and others known in the art. Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, propylene glycol stearate, and others known in the art. Suitable pH agents include hydrochloric acid, phosphoric acid, diethanolamine, triethanolamine, sodium hydroxide, monobasic sodium phosphate, dibasic sodium phosphate, and others known in the art. Suitable preservatives include benzyl alcohol, sodium benzoate, parabens, and others known in the art. The compounds of the present invention may be in powder form for constitution with a suitable vehicle, e.g., sterile pyrogen-free water, before use. The formulations of the present invention may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

In some embodiments, a compound of the present invention is prepared with a carrier that will prolong the activity of the compound such as a controlled release formulation, prevent or inhibit degradation or loss of activity, or prevent or inhibit loss of the compound due to factors such as metabolism. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically or cosmetically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from the cell culture assays and animal studies can be used in formulating a range of dosage for human use according to methods known in the art.

The following Examples are intended to illustrate, but not to limit the present invention.

The compounds used in the following examples are as follows: The NCI Diversity Set was obtained in 96-well plate format from the National Cancer Institute. See the World Wide Web at dtp.nci.nih.gov/branches/dscb/diversity_explanation.html, which is herein incorporated by reference. The syntheses of N,N-bis(7-chloroquinolin-4-yl)alkanediamines and N,N-bis(7-chloroquinolin-4-yl)heteroalkanediamines used herein is known in the art. See Vennerstrom, et al. (1992) J. Med. Chem. 35:2129-2137; and Vennerstrom, et al. (1998) J. Med. Chem. 41:4360-4364, which are herein incorporated by reference. Amodiaquine, chloroquine, quinacrine, quinidine, and quinine were obtained from Sigma-Aldrich (USA).

EXAMPLE 1

High Throughput Assay of BoNT/A LC Activity

The high throughput assay used to screen BoNT/A LC proteolytic activity is known in the art. See Schmidt, et al. (2001) Anal. Biochem. 296:130-137, which is herein incorporated by reference.

Briefly, liquid transfers were done with a SCICLONE® automated pipettor (Zymark, Hopkinton, Mass.). Recombinant BoNT/A LC was diluted to 0.6 ng/ml in 40 mM hepes, 0.5 mg/ml BSA, pH 7.4. See Ahmed & Smith (2000) J. Prot. Chem. 19:475-487. Test compounds were diluted to 0.2 mM with methyl sulfoxide. Ten µl of each compound were transferred into the corresponding wells of another 96-well plate containing immobilized fluorescent-labeled peptide substrate, specific for the protease activity of BoNT/A LC. See Schmidt, et al. (2001) Anal. Biochem. 296:130-137, which is herein incorporated by reference. Ninety µl BoNT/A LC were then added and mixed, for final concentrations of 20 µM compound and 0.5 ng/ml BoNT/A LC. Blanks (buffer only) and controls (buffer and BoNT/A LC), eight wells each, were included on each assay plate. After incubation at 30° C. for 60 minutes, 70 µl were transferred from each well to an opaque-wall plate, and fluorescence was measured in a WALLAC® 1420 multi-label counter (Perkin-Elmer, Gaithersburg, Md.).

Compounds exhibiting greater than about 40% inhibition in high-throughput assays were retested in a HPLC Based assay as described previously. See Schmidt & Stafford (2003) Appl. Environ. Microbiol. 69:297-303; and Schmidt & Bostian (1997) J. Prot. Chem. 16:19-26, which are herein incorporated by reference.

EXAMPLE 2

BoNT/A LC Refinement and Inhibitor Docking

The structure of BoNT/A LC was obtained from the deposited crystallographic coordinates of the holotoxin (PDB refcode=3BTA). See Lacy, et al. (1998) Nat. Struct. Biol. 5:898-902, which is herein incorporated by reference. The 3.2 Å holotoxin includes the heavy chain, light chain, and a protective residue belt that covers the substrate binding site of the light chain. The heavy chain and the protective belt were removed from the holotoxin, and the light chain was energy refined using the Discover (Accelrys Inc. San Diego, Calif.) program's cff91 force field. During the refinement, the zinc ion, and residues coordinating the zinc ion, were fixed in their original coordinates. Our strategy entailed applying 2,000 kcal/mol per Å$^2$ of force that was stepped off the structure in 100-kcal/mol decrements by minimizing with conjugate gradients, until the norm of the gradient was 0.01 kcal/Å. See Giannakakou, et al. (2000) PNAS 97:2904-2909, which is herein incorporated by reference. This process was repeated until all applied external force was removed. The resulting coordinates of the final model were within the experimentally determined x-ray crystallographic resolution. The optimized structure had an rms deviation of 2.6 Å across all backbone atoms from the reported crystallographic coordinates of the holotoxin light chain.

Using InsightII molecular modeling software (Accelrys, Inc., San Diego, Calif.), identified inhibitors were manually docked into the BoNT/A LC substrate binding cleft, and Van der Waals violations of 0.25 Å were removed by small adjustments to side-chain torsion angles and inhibitor positioning. The inhibitor-enzyme structure coordinates were subsequently tether minimized in the same manner as described above, and the final structure was subjected to hydropathic analysis using the program HINT (eduSoft, Richmond, Va.).

EXAMPLE 3

Conformer Generation

Conformational models of inhibitors were generated using Catalyst 4.7® software (Accelrys, Inc., San Diego, Calif.). Inhibitors were imported into Catalyst® and energy minimized to the closest local minimum using the generalized CHARMM-like force field, as implemented in the program. Following, the "best quality" conformational search option was employed to generate conformers within 20 kcal mol$^{-1}$ from the global energy minimum. In this study it was found that 100 conformers per compound ensured adequate coverage of conformational space.

EXAMPLE 4

Molecular Modeling

Michellamine B was obtained from the National Cancer Institute, and Q2-15 was obtained from Dr. Jonathan Vennerstrom, University of Nebraska Medical Center. The HPLC based assay used to quantitate BoNT/A LC inhibition is known in the art. See Schmidt & Stafford (2003) Appl. Environ. Microbiol. 69:297; and Schmidt & Bostian (1997) J. Prot. Chem. 16:19, which are herein incorporated by reference.

A. BoNT/A Holotoxin X-Ray Structure (PDB 3BTA)

The BoNT/A holotoxin X-ray structure (PDB 3BTA) includes both the HC and the LC. See Lacy, D. B., et al. (1998) Nat. Struct. Biol. 5:898, which is herein incorporated by reference. First, the HC was removed from the structure, and hydrogens were added to the LC. Following, the BoNT/A LC was energy refined using the Discover (Accelrys, San Diego, Calif.) program's cff91 force field. The zinc ion, and coordinating residues (H222, E223, H226, and E261) were fixed to their original crystallographic coordinates. The molecular mechanics energy refinement involved applying 2000 kcal/mol per $Å^2$ of force that was stepped off the structure in 100 kcal/mol decrements by minimizing with conjugate gradients until the norm of the gradient was 0.01 kcal/$Å^2$. See Giannakakou, P., et al. (2000) PNAS USA 97:2904; and Panchal, R. G., et al. (2004) Nat. Struct. Biol. 11:1, which are herein incorporated by reference. The coordinates of the energy-refined model were within the experimentally determined X-ray crystallographic resolution, and were used as a starting point for molecular dynamics simulations.

Molecular dynamics were performed using Discover 3.0, and involved 200 ps of direct velocity scaling (cff91 force field, distance dependent dielectric, 0.5 fs time step, initial temperature=10K, final temperature=300K), followed by 1 ns of production dynamics using the Berendsen method of temperature-bath coupling (0.5 fs time step; 300K; sample structures were collected at 250 fs increments). Initially, at least one hundred lowest energy structures and 10 highest energy structures were used to analyze BoNT/A LC conformers collected over the course of the Berendsen phase of the dynamics simulation.

B. BoNT/A Holotoxin X-Ray Structure (PDB 1E1H)

The X-ray structure PDB 1E1H is composed of two LCs engaged in the intermolecular autocatalysis of a peptide bond located in corresponding loops (composed of residues 231-259). See Segelke, B., et al. (2004) PNAS USA 101:6888, which is herein incorporated by reference. For these studies, one of the LCs and all water molecules were removed from the X-ray crystal structure; the LC composed of residues A7-A249 and B251-B415 was chosen for dynamics simulations. Several residues were missing from surface loops of the crystal structure: L199, E200, V201, D202, T203, N204, P205, L206, Y250 and N393. These missing residues were built into the structure using corresponding residues in the 3BTA BoNT/A LC as templates. Following, hydrogens were added and the 1E1H BoNT/A LC was subjected to the same molecular mechanics and molecular dynamics protocols described above (i.e., for the 3BTA BoNT/A LC). At least one hundred lowest energy structures and 10 highest energy structures from the production dynamics phase were used to analyze conformers of this BoNT/A LC.

Inhibitors were docked by combining molecular mechanics minimizations with the hydropathic scoring function HINT (eduSoft, Richmond, Va.) in an iterative manner to achieve optimal complementarity with BoNT/A LC substrate binding clefts. See Giannakakou, P., et al. (2000) PNAS USA 97:2904; and Panchal, R. G., et al. (2004) Nat. Struct. Biol. 11:1, which are herein incorporated by reference. Compounds were first manually docked into the BoNT/A LC substrate binding cleft, and Van der Waals violations equal to or greater than about 0.25 Å were removed by small adjustments to inhibitor positioning and enzyme side-chain torsion angles. The inhibitor-enzyme structure coordinates were minimized in the same manner as described above, and were subjected to hydropathic analyses, using the program HINT, to eliminate/reduce unfavorable contacts.

EXAMPLE 5

3D-QSAR & Pharmacophore Generation

The molecular modeling software, CATALYST® 4.7 software (Accelrys Inc., San Diego, Calif.) is used to construct a three-dimensional QSAR pharmacophore model for the activities exhibited by compounds that inhibit Botulinum neurotoxin A metalloprotease activity. A training set is used to construct the pharmacophore model.

The pharmacophore model is developed by placing suitable constraints on the number of available features such as, aromatic hydrophobic or aliphatic hydrophobic interactions, hydrogen bond donors, hydrogen bond acceptors, hydrogen bond acceptors (lipid), and ring aromatic sites to describe the activity of the compounds.

During this pharmacophore or hypothesis generation, the molecules are mapped to the features with their pre-determined conformations generated earlier using the "fast fit" techniques in the CATALYST®.

EXAMPLE 6

Cross Validation of Pharmacophore Model

The pharmacophore model may be cross-validated by generating a test set of different repellent compounds known in the art. The test set compounds may be screened for repellent activity in a manner identical to the compounds of the original training set according to Example 1 or methods known in the art. The compounds of the test set for cross validation should not be ones of the original training set used for automatic generation of the pharmacophore.

Regression analysis is performed by mapping this test set onto the features of the pharmacophore and should show remarkable consistency of the model (R greater than about 0.85, preferably greater than about 0.90, more preferably greater than about 0.95). Regression information is used to estimate activity of the training set of the compounds as well as to estimate the unknown compounds. The greater the fit of the pharmacophore with the compound, the more likely the compound will exhibit repellent activity. The regression for both the training set and the test set is calculated by the following equation:

$$-\log(\text{activity})_{Est}=\text{Fit}*\text{Slope}+Y \text{intercept}$$

See Catalyst® Tutorials, Release 4.5, August 1999, Accelrys Scientific Support. 9685 Scranton Road, San Diego, Calif. 92121-3752, which is herein incorporated by reference.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A method of inhibiting Botulinum neurotoxin A metalloprotease activity which comprises contacting a compound selected from the group consisting of
Michellamine B;
NSC 357756;
NSC 119889
NSC 86372;
NSC 130796;
NSC 402959;
Q1-3;
Q1-19;
Q1-21;
Q2-11;
Q2-15;
Q2-43;
Q2-59;
Q2-61;
Q2-97;
Q3-53;
Q3-81; and
Q3-87
with a Botulinum neurotoxin A metalloprotease to inhibit the Botulinum neurotoxin A metalloprotease.

2. The method of claim 1, wherein the compound is in a composition.

3. The method of claim 2, wherein the composition further comprises a pharmaceutically acceptable carrier.

4. The method of claim 2, wherein the composition further comprises at least one supplementary active compound.

5. A method of inhibiting Botulinum neurotoxin A metalloprotease activity which comprises
screening a plurality of existing small molecule compounds for a small molecule compound that inhibits Botulinum neurotoxin A metalloprotease activity; and has a first plane A, a second plane B, a first hydrophobic moiety C, a second hydrophobic moiety D and a positive ionizable substituent E, wherein one or both of the planes comprise a biaryl group or a triaryl group and
(a) the distance between the center of the first plane A and the center of the second plane B is about 6.5 to about 9.5 Å;
(b) the distance between the center of the first hydrophobic moiety C and the center of the second hydrophobic moiety D is about 8.0 to about 16.0 Å;
(c) the distance between the center of the first plane to the center of the first hydrophobic moiety C is about 3.0 to about 5.0 Å;
(d) the distance between the center of the second plane to the center of the second hydrophobic moiety C is about 3.0 to about 5.0 Å; and
(e) the distance between the center of the first plane to the center of the positive ionizable substituent is about 6.5 to about 9.5 Å; and
contacting the small molecule compound with a Botulinum neurotoxin A metalloprotease to inhibit the Botulinum neurotoxin A metalloprotease.

6. The method of claim 5, wherein the small molecule compound further comprises a heteroatom in the first plane A.

7. The method of claim 5, wherein the biaryl group is selected from the group consisting of naphthalene, quinoline, isoquinoline, benzofuran, indole, quinazoline, quinoxaline, naphthyridine, phthalazine, and purine.

8. The method of claim 5, wherein the triacyl group is selected from the group consisting of acridine, phenazine, phenanthroline, phenanthridine, and carbazole.

9. The method of claim 5, wherein the hydrophobic moieties are capable of occupying the binding subsites 1 and 2 of the BoNT/A LC substrate binding cleft.

10. The method of claim 5, wherein the hydrophobic moieties are each independently selected from the group consisting of an alkyl group, bromo, chloro, iodo, alkyoxy, and an unsaturated heterocycle.

11. The method of claim 5, wherein the positive ionizable substitutent is selected from the group consisting of a primary amine, a secondary amine, or a tertiary amine moiety attached to an aromatic ring.

12. The method of claim 5, wherein the compound is a bisquinoline.

13. The method of claim 5, wherein the compound is selected from the group consisting of
Michellamine B;
NSC 357756;
NSC 119889
NSC 86372;
NSC 130796;
NSC 402959;
Q1-3;
Q1-19;
Q1-21;
Q2-11;
Q2-15;
Q2-43;
Q2-59;
Q2-61;
Q2-97;
Q3-53;
Q3-81; and
Q3-87.

14. The method of claim 5, wherein the compound is in a composition.

15. The method of claim 14, wherein the composition further comprises a pharmaceutically acceptable carrier.

16. The method of claim 14, wherein the composition further comprises at least one supplementary active compound.

17. A method of inhibiting Botulinum neurotoxin A metalloprotease activity which comprises
screening a plurality of existing small molecule compounds for a small molecule compound that inhibits Botulinum neurotoxin A metalloprotease activity and has a first plane A, a second plane B, a first hydrophobic moiety C, a second hydrophobic moiety D and a positive ionizable substituent E, wherein one or both of the planes comprise a biaryl group or a triaryl group and
(a) the distance between the center of the first plane A and the center of the second plane B is about 6.5 to about 9.5 Å;
(b) the distance between the center of the first hydrophobic moiety C and the center of the second hydrophobic moiety D is about 8.0 to about 16.0 Å;
(c) the distance between the center of the first plane to the center of the first hydrophobic moiety C is about 3.0 to about 5.0 Å;
(d) the distance between the center of the second plane to the center of the second hydrophobic moiety C is about 3.0 to about 5.0 Å; and
(e) the distance between the center of the first plane to the center of the positive ionizable substituent is about 6.5 to about 9.5 Å; and
contacting the small molecule compound with a Botulinum neurotoxin A metalloprotease to inhibit the Botulinum neurotoxin A metalloprotease, wherein the small molecule further comprises a heteroatom in the first plane A;

wherein the biaryl group is selected from the group consisting of naphthalene, quinoline, isoquinoline, benzofuran, indole, quinazoline, quinoxaline, naphthyridine, phthalazine, and purine;

wherein the triacyl group is selected from the group consisting of acridine, phenazine, phenanthroline, phenanthridine, and carbazole;

wherein the hydrophobic moieties are capable of occupying the binding subsites 1 and 2 of the BoNT/A LC substrate binding cleft;

wherein the hydrophobic moieties are each independently selected from the group consisting of an alkyl group, bromo, chloro, iodo, alkyoxy, and an unsaturated heterocycle;

wherein the positive ionizable substitutent is selected from the group consisting of a primary amine, a secondary amine, or a tertiary amine moiety attached to an aromatic ring; and wherein the compound is a bisquinoline.

* * * * *

UNITED STATES PATENT AND TRADEMARK OFFICE
CERTIFICATE OF CORRECTION

PATENT NO. : 7,574,340 B2
APPLICATION NO. : 10/935622
DATED : August 11, 2009
INVENTOR(S) : Bavari et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 277 days.

Signed and Sealed this

Seventh Day of September, 2010

David J. Kappos
*Director of the United States Patent and Trademark Office*